(12) United States Patent
Lüdicke et al.

(10) Patent No.: US 10,648,993 B2
(45) Date of Patent: May 12, 2020

(54) LABORATORY APPARATUS WITH USER INPUT FUNCTION AND METHOD FOR USER INPUT IN A LABORATORY APPARATUS

(71) Applicant: EPPENDORF AG, Hamburg (DE)

(72) Inventors: Sven Lüdicke, Hamburg (DE); Martin Poggenclaas, Hamburg (DE); Stefan Roth, Hamburg (DE); Kirsten Schicke, Kaltenkirchen (DE)

( * ) Notice: Subject to any disclaimer, the term of this patent is extended or adjusted under 35 U.S.C. 154(b) by 52 days.

(21) Appl. No.: 15/118,362

(22) PCT Filed: Feb. 12, 2015

(86) PCT No.: PCT/EP2015/000311
§ 371 (c)(1),
(2) Date: Aug. 11, 2016

(87) PCT Pub. No.: WO2015/120986
PCT Pub. Date: Aug. 20, 2015

(65) Prior Publication Data
US 2017/0176479 A1    Jun. 22, 2017

(30) Foreign Application Priority Data
Feb. 14, 2014  (EP) .................................. 14000534

(51) Int. Cl.
*G01N 35/00* (2006.01)
*G06F 3/0488* (2013.01)
(Continued)

(52) U.S. Cl.
CPC .......... *G01N 35/00722* (2013.01); *B01L 3/02* (2013.01); *B01L 3/0237* (2013.01);
(Continued)

(58) Field of Classification Search
CPC ....... G01N 35/00722; G01N 35/00584; G01N 33/48785; G01N 2035/0091;
(Continued)

(56) References Cited

U.S. PATENT DOCUMENTS

2014/0046484 A1    2/2014  Glauser et al.
2015/0314246 A1*  11/2015  Lehtonen ............ B01F 13/0818
                                                       700/265

FOREIGN PATENT DOCUMENTS

CN          202171795 U     3/2012
WO     WO 2010/076772 A2    7/2010
(Continued)

OTHER PUBLICATIONS

Applied Biosystems 7500/7500 Fast Real Time PCR System; Part No. 4387779 Rev. C; Jun. 2010; pp. vii-xxii and 1-123 (Year: 2010).*

(Continued)

*Primary Examiner* — Benjamin R Whatley
(74) *Attorney, Agent, or Firm* — Todd A. Lorenz

(57) ABSTRACT

The invention relates to a laboratory apparatus, and a method, for device-controlled handling of at least one laboratory sample, wherein the laboratory apparatus comprises at least one handling device, wherein the handling is controlled by the laboratory apparatus in use of several program parameters, a control device, a user interface device for manually inputting data by an user, and for the display of information, which may in particular depend on these data, wherein the user interface device comprises a display, on which a display area can be represented, and wherein the user interface device comprises a movement detecting sensor device, which is arranged for the detection of at least one user movement, which can be performed on the display area by an user, and wherein the control device is arranged for the provision of a movement detecting input mode, in order (Continued)

to•select the at least one program parameter and/or define its value depending on the at least one user movement, and•display at least one graphical sketch element, which represents the at least one user movement, in the display area, depending on the at least one user movement.

13 Claims, 10 Drawing Sheets

(51) Int. Cl.
| | |
|---|---|
| *G06F 3/0484* | (2013.01) |
| *B01L 7/00* | (2006.01) |
| *B01L 3/02* | (2006.01) |
| *G01N 33/487* | (2006.01) |
| *G06F 3/01* | (2006.01) |
| *G06F 3/0482* | (2013.01) |

(52) U.S. Cl.
CPC .............. *B01L 7/52* (2013.01); *G06F 3/0488* (2013.01); *G06F 3/04847* (2013.01); *G06F 3/04883* (2013.01); B01L 2200/087 (2013.01); B01L 2300/027 (2013.01); G01N 33/48785 (2013.01); G01N 35/00584 (2013.01); G01N 2035/0091 (2013.01); G06F 3/017 (2013.01); G06F 3/0482 (2013.01); G06F 3/04842 (2013.01)

(58) Field of Classification Search
CPC .... B01L 3/0237; B01L 7/52; B01L 2200/087; B01L 2300/027; G06F 3/04847; G06F 3/04883; G06F 3/017; G06F 3/0482; G06F 3/04842; G06F 3/0488
See application file for complete search history.

(56) References Cited

FOREIGN PATENT DOCUMENTS

| WO | WO 2012/045415 A1 | 4/2012 |
|---|---|---|
| WO | WO 2013/106527 A1 | 7/2013 |
| WO | WO 2014/015186 A1 | 1/2014 |
| WO | WO 2014/090687 A1 | 6/2014 |

OTHER PUBLICATIONS

Biomek 3000 Laboratory Automation Workstation; Beckman Coulter, Quick Start Guide; Part No. 987837, revision AD; Dec. 2009; pp. i-vi and 1-1 through 3-18 (Year: 2009).*

Relative Quantification (Getting Started Guide, Relative Quantification. Applied Biosystems 6300/7500 real time PCR System, part No. 4375799, Rev E, pp. ii-viii, and 1-60, published Jun. 2010; hereinafter "Relative Quantification").*

Applied Biosystems Veriti Thermal Cycler, User Guide; part No. 4375799, Rev E, pp. ii-viii, and 1-60, published Jun. 2010 (Year: 2010).*

Villamor et al., "Touch Getsture Reference Guide," Apr. 15, 2010; URL:http://static.lukew.com/TouchGestureGuide.pdf (retrieved on Jul. 7, 2014).

"G-Storm-2011 G-Storm GS4M Instruction Manual,", pp. 1-61, Dec. 31, 2011; URL:http//www.gstormdirect.com/wp-content/uploads/GS4M-user-manual-V1AG.pdf (retrieved on Jul. 7, 2014).

"G-Storm Thermal Cyclers," pp. 1-16, May 13, 2012; URL:http://www.labtec.fr/system/files/Brochure_Labtech_Gstorm.pdf (retrieved on Jul. 7, 2014).

* cited by examiner

LABORATORY APPARATUS WITH USER INPUT FUNCTION AND METHOD FOR USER INPUT IN A LABORATORY APPARATUS

The invention relates to laboratory apparatus having user input function, and method for a user input in a laboratory apparatus.

Such laboratory apparatuses are used, in order to process laboratory samples, in particular liquid laboratory samples, in chemical, biological, biochemical, medical or forensic laboratories with high efficiency. Laboratory apparatuses like this automate handling steps at least partially, which would otherwise be performed manually, and in this way increase the speed, precision and reliability of these handlings. A handling of mostly liquid laboratory samples may be directed to change or to analyze these laboratory samples, in particular their composition, physically, chemically, biochemically or in another way.

A handling of a liquid laboratory sample may be directed to change this sample in its composition physically, chemically, biochemically or in another way. By the handling of the sample, a sample can e.g. be divided or diluted. The ingredients of a sample can be analyzed or one may produce new ingredients by a chemical reaction, in particular in use of the sample. In particular, laboratory apparatuses are helpful in connection with the processing and analysis of DNA or RNA or their components, in order to gain a wealth of information within an appropriate period of time or to analyze plenty of such samples.

The mentioned laboratory apparatuses comprise one or more handling device(s) for device-controlled handling of at least one laboratory sample. They often comprise a program control by means of which a user of the laboratory apparatus can define the handling to be performed by setting of the desired program parameters. The setting of the program parameters occurs via an operating unit of the laboratory apparatus, which enables the input and output of information, particularly of values of program parameters.

The programming of established laboratory apparatuses was often described as uncomfortable and not very user-friendly. Occasionally, extensive numerical inputs had to be made by means of a keyboard or other input means by the user, before all program parameters necessary to be entered for the automatic processing of a sample handling by the user were inputted and the sample handling could be started.

It is an object of the present invention to provide an improved laboratory apparatus having a user input function and to provide an improved method for the user input in a laboratory apparatus, with which productivity in a laboratory can be improved.

The invention particularly solves this problem by the laboratory apparatus according to claim 1 and the method according to claim 13. Preferred embodiments are in particular objects of the dependent claims.

The laboratory apparatus for device-controlled handling of at least one laboratory sample according to the invention comprises: —at least one handling device for program-controlled handling of the at least one laboratory sample, wherein the handling using several program parameters, which are at least partly defined as user parameters by a user, are controlled by the laboratory apparatus, —a control device, comprising at least one processor device for data processing, wherein this data processing includes the execution of a control program for controlling the laboratory machine, and comprising at least one storage device for storing data, in particular the control program and the program parameters, —a user interface device configured for the manual input of data by a user, and for the display of information, which in particular may depend on these data, wherein the user interface device comprises a display, on which a display area can be displayed, and wherein the user interface device comprises a movement detecting sensor device, which is arranged for the detection of at least one user movement, which is performable on the display area by a user, and wherein the control device is arranged for the provision of a movement detecting input mode, in order to•select the at least one program parameter and/or define its value depending on the at least one user movement, and•display at least one graphical sketch element, which represents the at least one user movement, in the display area, depending on the at least one user movement.

The handling device is one of the following devices or comprises at least one of the following devices:

a laboratory centrifuge, a laboratory centrifuge comprising at least one of the following components: a rotor, a drive device, a heating/cooling device, a timer device, by means of which time parameters of the rotation or temperature setting can be controlled;

a thermal cycler, a thermal cycler comprising at least one of the following components: a thermal block, a control device with at least one control loop, to which at least one heating/cooling device is assigned as an actuator and at least one temperature measurement device is assigned as a measurement element, heating and/or cooling elements, a timer device, by means of which time parameters for setting the temperature cycle can be controlled;

a laboratory spectral photometer, a laboratory spectral photometer comprising at least one of the following components: a light source, a timer device for timing the sequence of a light, a photodetector;

a cell counter, a cell counter comprising at least one of the following components: a light source, an image acquisition unit, an image evaluation unit, a positioning device;

a laboratory incubator, a laboratory incubator comprising at least one of the following components: a timer device for timing a sequence of an incubation handling program consisting of several steps, the timer device being, in particular, a timer switch, a heating/cooling apparatus, a setting device for the control of the substitute gas supplied to an incubator chamber of the laboratory incubator, an incubator chamber, a control device having at least one control loop, to which at least one heating/cooling device is assigned as an actuator and at least one temperature measurement apparatus is assigned as a measurement element;

a laboratory shaker, a laboratory shaker comprising at least one of the following components: a drive of for driving the shaking movement, a timer device, by means of which time parameters of the setting of the shaker handling can be controlled, a heating/cooling device, a control device with at least one control loop, which is assigned the at least one heating/cooling apparatus as actuator and at least one temperature measurement apparatus as measurement element;

a laboratory mixing device, a laboratory mixing device comprising at least one of the following components: a drive for driving the mixing movement, a timer device, by means of which time parameters of the setting of the mixer handling can be controlled, a heating/cooling device, a control device with at least one control loop, which is assigned to at least one heating/cooling apparatus as actuator of the laboratory mixing device and at least one temperature measurement apparatus as measurement element;

a freezer, a freezer comprising at least one of the following components: a cooling device, a control device having at least one control loop, to which at least one cooling device of the laboratory freezing device is assigned as an actuator and at least one temperature measurement device is assigned as a measurement element of the laboratory freezing device, a control measurement device for measuring the temperature, an alarm device, by means of which an alarm signal is emitted, if the temperature measured in the freezer space leaves a permitted temperature range; an information reading device for reading an information related to the at least one laboratory sample, the information being contained in an information medium, e.g. an RFID chip, which is connected to a sample container, which contains the at least one laboratory sample;

a bioreactor, a bioreactor comprising at least one of the following components: a stirring device for stirring the sample contained within the reactor container, a pumping device for pumping the laboratory sample, setting device for setting a gas content in a reactor container, a setting device for setting, in particular controlling, a pH value in the sample in the reactor container, a biological safety workbench, a biological safety workbench comprising at least one of the following components: a conveying device for conveying atmospheric gas, a timer device for measuring a filter operation duration and fan operation duration, a measurement device for measuring a conveyed amount of atmospheric gas;

a sample plate reading device, a sample plate reading device comprising at least one of the following components: a light source or radiation source, a photodetector, a temperature control device for the tempering of the samples or the sample plates, a timer device for measuring a time duration;

laboratory machine for handling fluid samples being a pipetting machine, laboratory machine for handling fluid samples being a pipette machine and comprising at least one of the following components: a transport device, for transporting sample containers or for transporting samples by guidance of samples through tube systems, capillaries or pipetting tips, a pipetting head, which comprises a connection section for the connection of one or more pipette tips; a workstation containing another handling device as described in the present specification, for example a thermal cycler comprising a thermal block.

A graphical sketch element may be a continuous graphical object, e.g. a path without interruption, in particular a continuous, partially or completely curved or not curved—i.e. straight—line or rather a curve with or without linear segments, or may be a discontinuous graphical object, e.g. path with interruption, in particular a sequence of two or more or many points, each point may be represented by a discrete graphical symbol, such as a square, rectangle, circle, cross, etc.

The laboratory apparatus, in particular the control program, is arranged for performing the handling of at least one laboratory sample as a function of the at least one program parameter, which is selected by the user movement and/or whose value is determined by this user movement. In this way, the user movement is made effective as input activity, similar to the pressing of a button or to the movement of a computer mouse or of a joystick. The graphical representation of the user movement in the display area of the display preferably occurs substantially without an observable time delay for the user, so that the user receives a visual feedback, and thus receives a visual monitoring of its user movement. In this way, the use of the laboratory apparatus is intuitive. In particular, program parameters can be inputted intuitively on the laboratory apparatus in this way. In this way, the operation is significantly facilitated; in particular a more efficient workflow can be achieved due to the more intuitive control system.

This movement controlled input is preferably feasible, if the user-interface device has been set to an input mode by an event, and is preferably not feasible, if the user interface device has not been set to an input mode. This prevents that unwanted inputs are performed at the display area. The mentioned event may be defined by the control program, e.g. by operating of the control program as a software operating system of the laboratory apparatus, which executes a program, in particular a sub-program or program module, or a method program. During the execution of this program, events initiating the input mode are activated, when a user input shall take place by user movement. Likewise, the input mode can be terminated program-controlled. But it is also possible and preferred that the user controls the starting and/or stopping the input mode by means of inputs, which he carries out over the user interface. Further, the starting and/or stopping of the input mode may also occur by means of a remote control, which can be realized by means of a data interface, which may be formed for wired or wireless data communications, unidirectional or bidirectional.

In this context, it is also preferred that—preferably at the same time during the input mode—further user inputs occur at the user interface, e.g. by pressing the hardware input means, e.g. of buttons, input fields, operating wheels or control pads, or virtual input devices, e.g. input fields, which can be displayed on a display area of a touch-sensitive display (touch screen). It is possible and preferred that by means of the user movement a program parameter is initially selected, preferably the value of this program parameter is set from this or any other—in particular direct or consecutively staggered in time—user movement, and that preferably subsequently the possibility is offered to the user to change, in particular to readjust, the value entered by means of the user movement. This can be done by a re-control of the movement and/or by the actuation of hardware input means. The mentioned functions of the laboratory equipment are preferably computer implemented. They can in particular be realized in that the control program, in particular the sub-programs, program modules or method programs preferably used by that, are correspondingly formed, in particular programmed, in order to enable control of the laboratory apparatus for the performance of the respective functions. This also applies to the preferred functions and capabilities of the laboratory apparatus according to the invention further described in the patent application, if technically feasible and if not stated otherwise.

The movement-detecting sensor device preferably is the touch-sensitive layer of the display, which is preferably configured as a touch screen. In this context, a contact may occur by a finger of the user or by means of an input help guided by the user, e.g. a stylus. The movement-detecting sensor device may also be arranged for contactless detection of the user movement. For this, the sensor device may in particular comprise at least one camera, in particular an infrared camera, by means of which recordings carried out from user movements on the display area can be established. These recordings can be evaluated, in particular by the user interface control, particularly by means of image processing programs, in order to detect the user movement. Preferred techniques for movement detection, particularly touch screens and in particular non-contact operating sensor devices, offer the advantage of a low friction or friction-free interaction of the user, which is thus considered to be particularly ergonomic.

A user interface device, particularly a touch screen, provides an input interface and an output interface between the laboratory apparatus and an user. The control device of the laboratory apparatus may include the control means for the control of the user interface device, which is also referred to as an user interface control. In this case, both the functions of the control of the at least one handling device and the user control on the user interface device are performed by the control device, in particular by means of a single data processing device, in particular a microprocessor device. However, the control device of the laboratory apparatus and the user interface control can also be configured as separate components, which each particularly comprise an own data processing device, in particular a microprocessor.

The control device and/or the user interface control are preferably arranged for receiving electrical signals from a touch screen or to send these to the latter. The display, in particular the touch screen, displays visual outputs to the user. The visual output may comprise different output elements, including e.g. graphics, in particular raster graphics or vector graphics, text, icons, video, and any combination thereof.

In particular, a touch screen may comprise the movement-detecting sensor device. A touch screen has a touch-sensitive surface, a sensor or a group of sensors that accepts inputs from a user based on haptic and/or tactile contact. The touch screen together with the user interface control in particular detect the contact, in particular the movement or the interruption of the contact, on the touch screen and interprets, in particular the detected contact, as an interaction of the user with input areas, which may in particular be arranged in the display area and may in particular be observable for the user. Preferably, a point of contact between a touch screen and the user corresponds with the fingertip of the user.

The touch screen can in particular use LCD (liquid crystal display) technology, or LPD (light emitting polymer display) technology. The touch screen and the user interface control can detect contact and movement or interruptions thereof. The sensor device preferably employed in this context can use a capacitive, resistive, infrared or acoustic surface-wave technology, as well as other short range sensor fields. The touch screen can e.g. have a resolution of preferably greater than 60 dpi or 100 dpi, in particular between 60 dpi and 350 dpi or between 100 dpi and 250 dpi. The user may contact the touch screen using an appropriate object or body portion, such as a stylus, a finger. The user interface control may particularly be arranged for transmitting the rough finger-based inputs into a precise position or movement of an object displayed on the display area, e.g. cursor, mouse cursor, icon, graph, etc.

A user interface device can be a component of the laboratory apparatus, which may be an integral part of the laboratory apparatus or, in an alternative embodiment, which can be operated separately from the laboratory apparatus, as it communicates with the control device of the laboratory apparatus by means of an interface device, in particular via electrical contacts or wireless. A user interface device, which is in particular also operable independently of the laboratory apparatus, can in particular have its own data processing device, and in particular have its own energy source, e.g. battery. The user interface device may in particular be configured as a mobile computing apparatus, in particular a tablet computer or a smart phone. This mobile computer apparatus is preferably arranged for the communication with the laboratory apparatus, e.g. by means of suitable software and/or interface device. This mobile computer apparatus may be configured as a separate commercially available tablet computer or as a separate commercially available smart phone or may be configured as a separate not commercially available tablet computer or not commercially available smart phone. The mobile computer apparatus may be arranged to be used as a user interface device for more than one laboratory apparatus, in particular for more than one handling specific type of laboratory apparatus.

It is possible and preferred that at least one program parameter is selected by the user movement. The laboratory device in particular detects from the user movement, which program parameter is selected by the user movement of the user. For explanation, reference is made to the exemplary embodiments: in a user movement, which is performed as a vertical line gesture, a laboratory apparatus according to the invention configured as a thermal cycler preferably identifies that the user has selected the program parameter "cycle time". In a user movement, which is performed as a horizontal line gesture, the laboratory apparatus preferably identifies that the user has selected the program parameters "cycle temperature". Preferably, the same input can be interpreted from the laboratory apparatus in a way that it defines a value for the selected program parameter. According to the example, e.g. the horizontal position of the vertical movement on the display area by the user defines the value of the program parameter "cycle time", the vertical position of the horizontal movement on the display area by the user determines the value of the program parameter "cycle temperature".

As an alternative to a user movement, which defines both the selection of the program parameter and the value of the program parameter at the same time, one may also use a first input of the user, in particular by means of a user movement, in order to perform the selection of the program parameter. A second input, in particular a second user movement, which can in particular be detected directly or at a time interval after the first input, can then define the value of the selected program parameter.

The user movement is preferably a gesture. A gesture is in particular defined in that it is understood as a movement of a body, which comprises information. However, a gesture can also be defined so that it is understood e.g. a certain body configuration, e.g. hand position, which includes the information. A gesture can be a single object gesture or a multi-object gesture. A single object gesture takes in particular account of only the movement of a single reference point, e.g. the point of contact of the fingertip of a user on the display area of the touch screen or the movement of a single hand in the detection area of a contactless operating sensor device on the display area. A multi-object gesture may evaluate several, preferably two, simultaneously moving reference points, e.g. the contact points of several fingertips or two hands.

A gesture may be a movement of the reference point along a predetermined movement path, which can in particular be determined in its direction and/or in its length. Preferably, less than 5, 10 or 15 gestures are provided, which can be distinguished easily. Preferably, these are rectilinear gestures, in particular horizontal or vertical gestures, or oblique rectilinear gestures, in particular approx. 45° gestures, wherein the length of the movement is preferably not evaluated. Preferably, these gestures are also combinations of various rectilinear sections, for example angular gestures, which may e.g. comprise a vertical and a horizontal portion that can in particular be distinguished in their relative orientation yet. Preferably, these gestures are also curved trajectories, e.g. a circular, curved, eight-shaped, and the like.

Preferably, the control device is arranged for graphically displaying information in the display area of the display, in particular information regarding at least one program parameter.

In a preferred input mode, potential values of a first program parameter, e.g. a time value, are displayed along a first linear axis. Preferably, the control device is arranged for detecting a user movement in this input mode perpendicular to the one first linear axis, in order to select the program parameter associated with this axis and/or to define its value. Preferably, the control device is arranged for detecting a user movement perpendicular to the one first linear axis in this input mode, in order to select the value of the program parameter that is associated with this axis. In this context, a position of the linear, vertical user movement along the first linear axis can in particular be detected, wherein this position is characteristic of this value. It is also possible that several user movements are detected sequentially in time, in particular sequentially in predetermined time intervals, e.g. at intervals from 0.0 to 3.0 seconds, or simultaneously, in order to e.g. detect several horizontal positions along that axis.

In this preferred input mode, potential values of at least a second program parameter, e.g. a temperature, are displayed preferably along a second linear axis. Preferably, the control device is arranged for detecting a user movement perpendicular to the one second linear axis in this input mode, in order to select the program parameter associated with this axis and/or to define its value. Preferably, the control device is arranged for detecting a user movement perpendicular to the one second linear axis in this input mode, in order to select the value of the program parameter associated with this axis. In this context, in particular a position of the linear, vertical user movement along the second linear axis can be detected, wherein this position is characteristic for this value. It is also possible that several user movements are detected sequentially in time or simultaneously, in order to e.g. detect several horizontal positions along that axis.

It is possible and preferred that the control device is arranged in that the input of a value occurs with a continuous local resolution by the detection of the position of the user movement that is perpendicular to the linear axis, wherein the resolution may e.g. be technically limited by the spatial resolution of the sensor device. However, it is also possible and preferred that the control device is arranged for providing the input of a value by the detection of the position of the user movement perpendicular to the linear axis with a reduced spatial resolution, in particular incrementally. For this purpose, the control device may detect the values at predetermined intervals, referred to as increments, which can limit the resolution of the detection of the values. The reduced spatial resolution may in particular be less than the spatial resolution of the sensor device, in particular, if it makes sense depending on the application. In chemical reactions, e.g. in a PCR, a spatial resolution of the representation, which corresponds to a time resolution of 10 seconds at the definition of a PCR cycle or corresponds to a temperature resolution of 0.1° C., can be useful.

In the preferred input mode, the first and second axis are oriented preferably perpendicular to each other. Preferably, the display is configured to be substantially rectangular having two substantially extending horizontal edges and two extending edges, which are substantially perpendicular to the horizontal edges. In this case, the first axis preferably extends horizontally and the second axis preferably extends perpendicular to the horizontal, e.g. vertical. In such a display particularly efficient processes can be represented, in which a process parameter, e.g. a temperature, can be represented over a flow parameter, which e.g. represents a time value or a position in a sequence. Typically, the flow parameters can be applied horizontally, preferably parallel to the x-axis of a Cartesian coordinate system, and the process parameters can be applied perpendicular thereto, parallel to the y-axis of the coordinate system.

Preferably, the control device is arranged for detecting pairs of program parameters or pairs of values of a program parameter or of two program parameters by the user movement. A multiplicity of such pairs can be represented graphically using dots or a curve, which are plotted on linear axes oriented perpendicular to each other, for example in a Cartesian coordinate system. The control device may be arranged to represent such a coordinate system in the display area. The control device may be arranged for evaluating a user movement, which is performed on the display area and which is represented in this coordinate system as a curved graphical sketch element, in order to detect in this coordinate system pairs of program parameters or pairs of values of a program parameter or of two program parameters. Preferably, the control device is configured in that the user may change individual curve sections subsequently and thus can change the pairs of program parameters or pairs of values of a program parameter or of two program parameters subsequently, as the inputs from other input means of the user-interface device are detected, or as a further user movement is evaluated at the display area. Another user movement can e.g. contact a segment of the curve, which represents the first user movement, in the display area and then in particular displace to another display area, in particular continuously or incrementally. In this way, a process planning in an automated PCR process may in particular occur intuitively, as will be explained with reference to the Figures.

Preferably, the control device is arranged for displaying several graphical objects in the display area and for using a substantially circular user movement, which contacts and/or reframes the at least one—preferably several—of these graphical objects, as a selection movement. In particular, it is feasible that each graphical object is associated with a program parameter and that the selection movement effects in that at least one program parameter, preferably several program parameters, are selected. For example, the control device in the display area may represent several subareas graphically, wherein each subarea represents a program parameter.

A first subarea can e.g. stand within the scope of the planning of a PCR process for the process parameters "first temperature", a second subarea can stand for the process parameter "second temperature", a third subarea can stand for the process parameter "third temperature", wherein these subareas can e.g. be represented horizontally side by side. A selection movement, the representation of which as a graphical sketch element contacts at least a, e.g. one, two or three of these subareas, may accordingly select at least one, in particular one, two or three of the program parameters; the control device may be configured to detect another input of the user, by which the program parameters, namely temperatures, selected by means of selection movement—or to be selected subsequently—are assigned to a temperature cycle, which then shall be repeated, e.g. according to a number of repetitions, which is to be inputted. In this way, process planning may be facilitated by means of selection movement.

It is also possible and preferred—in particular in the execution of laboratory apparatus as a pipetting machine—that in the display area, a working area of the laboratory apparatus is represented graphically, in which several work stations are arranged, namely preferably grid-shaped. A laboratory apparatus having several work stations can, e.g. comprise several handling devices that are used in an automated process in a specific order. In a pipetting machine, e.g. samples and lab ware, in particular single or multiple sample vessels, pipette tips, liquid storages, tools, are stored at predetermined work stations of the working area. In other work stations, samples are pipetted, temperature-handled in particular in case of a PCR cycles temperature-handled, magnetically handled, mixed, irradiated, etc. By the graphical representation of the working area and the graphically assisted selection of program parameters according to the invention, e.g. a process may be planned at several work stations and in an intuitive way. A first subarea represented in the display area then represents e.g. a first work station, a second subarea represents a second work station, a third subarea represents a third work station, an nth subarea represents an nth work station (n=1 ... N, N is a natural number). At least one program parameter or a certain value of a program parameter can be associated with a—in particular each—subarea. The control device is configured to detect a user movement, the representation of which as a graphical sketch element on the display area contacts at least one or at least two subareas, and thereby selects at least one program parameter, which is associated with this subarea. By the user movement, several work stations can be selected, in particular can be connected in an order, which e.g. may correspond to the order in which a continuous user movement contacts these subareas. In this way, work stations—in particular the order of their use in a handling process—can be defined. For the user, there is the advantage of an efficient process planning.

In a pipetting machine, a further preferred embodiment ensues. The input by user movement can be used, in order to define a pipetting pattern in a laboratory apparatus, which is configured as a pipetting machine according to the invention. A pipetting machine comprises at least one working area having at least one or more work stations. The work stations are either automatically or manually equipped with laboratory vessels, e.g. with individual vessels, e.g. PCR tubes, or multiple laboratory vessels, e.g. microtiter plates. The laboratory vessels will also be filled at least partially with liquid laboratory samples in an automatic or manual way. Then it may be the object of the pipetting machine to pipette, according to a defined pipetting pattern, the liquid laboratory samples from a first quantity of laboratory vessels in a second quantity of laboratory vessels according to a pipetting pattern, which is to be defined by the user. The first and second quantity of laboratory vessels may comprise one or several laboratory vessels in each case.

The control device is preferably arranged for representing in the display area a first quantity of graphical symbols that represent a first quantity of laboratory vessels, and for representing a second quantity of graphical symbols that represent a second quantity of laboratory vessels, wherein the first quantity and the second quantity of symbols are in particular spaced from each other. The control device is preferably arranged for detecting an user movement, the representation of which as a graphical sketch element contacts the first quantity of graphical symbols and also a second quantity of graphical symbols, so that the first and second quantity of graphical symbols are connected to each other graphically by the graphical sketch element. The control device is preferably configured in this way to define program parameters and/or their values, which define in case of automated pipetting, according to which pipetting pattern the liquid samples from the first quantity of laboratory vessels—namely sucking the first laboratory samples in at least one liquid transfer tool, e.g. at least one pipette tip—are pipetted in the second quantity of laboratory vessels, namely delivering the laboratory samples from the at least one fluid transfer tool in the second quantity of laboratory vessels. The pipetting pattern may provide several fluid transfers of laboratory samples from a first quantity of laboratory vessels in a second quantity of laboratory vessels. The control device is preferably arranged for detecting several user movements successively, which each may represent at least one pipetting procedure.

Preferably, the control device or the user interface control possesses a gesture database, in which the gesture information are stored for the identification of predetermined gestures, in particular referred to as gesture data. The gesture database can be stored in a storage device of the control device. Preferably, the control device or the user interface control is arranged for investigating the movement information from this user movement, in particular in the form of movement data.

Preferably, the control device or the user interface control possesses correlation data within gesture data and other parameters, in particular program parameters. This correlation data may be stored in the storing device, in particular in a database, in particular in the gesture database. This correlation preferably occurs depending on the context, i.e. depending on the status of the control program of the laboratory apparatus, a correlation between gesture and parameter connected thereby is preferably carried out. The status can e.g. be determined by the input mask displayed to the user in the display area or by a specific input mode, during which the detection of user movements may exclusively be enabled. This input mask may vary depending on the program execution of the control program or rather the program module or method program or rather depending on the status of its eradication. As a result, a vertical gesture may cause the selection of a time parameter and the definition of its value during a first condition of the control program, whereas the same vertical gesture may cause the selection of a location parameter and setting its value during a second condition of the control program.

The movement data may be stored in a storage device of the control device for short-term or for long-term, in particular the control device may be configured to relate specific movement data to an user identified before—in particular by means of an authentication procedure—and to store these together with the identity of the user as an user dataset.

Preferably, the control device is configured to execute a gesture training procedure, which requires the performance of predetermined gestures at the laboratory apparatus by an individual user or by an administrator of the laboratory apparatus. For this purpose, at least one movement pattern to be reproduced is displayed to the user in the display; this movement pattern is then reproduced by the user, wherein the user movements are detected and stored as user-dependent movement data. By means of such a gesture training process, gesture recognition probability can be optimized, with which a user movement is correctly identified as a specific gesture. The reason is that the gestures of people is, similar to the language or handwriting, an individual property, the individual evaluation of which may be outmatched to an user-unspecific evaluation.

Alternatively or in addition to the gesture training method described above, a further gesture training process can be used, with which the user—and preferably each user—at least once or several times is trained for the performance of a predetermined gesture, until he is certified for gesture input on the laboratory apparatus. For this purpose, a gesture can once or repeatedly given and reproduced by the user, until the detection is sufficiently secure.

The movement information is in particular adapted to be compared with the gesture information. Preferably, the control device or the user interface control is arranged to compare the movement information with gesture information. The result of this comparison can determine, whether a predefined gesture is substantially recognized clearly or was identified with a certain probability. The result of this comparison can specify which predefined gesture was performed by the user.

A control device within the scope of the present invention generally comprises in particular a data processing device, in particular a computing unit (CPU) for processing data and/or a microprocessor or is a data processing device. A computing unit of the control device of a laboratory apparatus is preferably also arranged to control the handling process and/or the individual handlings.

The term "handling" in particular means that a laboratory sample, which is mostly liquid, is moved, and/or transported, and/or analyzed and/or modified, particularly is modified in its composition, physically, chemically, biochemically or otherwise.

The control device of the laboratory apparatus and/or the user interface device can—in particular all—be integrated into a physical device unit, but each may also be a separate physical device unit. A physical device unit can in particular be a module that is connected or can be connected to the laboratory apparatus. The control device of the laboratory apparatus and/or the user interface device or parts of these components may be implemented by software functions, or can in particular be existent as a program code. A laboratory apparatus can e.g. comprise a computer, which at least partially implements in each case the control device of laboratory apparatus and/or the user interface device in combination with software functions. In case that e.g. the user interface device is integrated into the laboratory apparatus, the user interface device can partly itself be part of the control device of the laboratory apparatus or rather be partially implemented by means of the control device, in particular by software functions, in particular at least partially as an executable program code.

A module can in particular comprise the user interface device. A module is a device separated from other devices and/or can be separated from the other device, which is in particular a laboratory apparatus. A laboratory apparatus may comprise a connection device, by which the module can be connected to the laboratory apparatus, in particular by means of a connection, which is configured to be releasable by the user. A module can be portable, and thus can be transported by a user. The module can also be permanently connected to the laboratory apparatus. The modular construction provides advantages in the manufacture of laboratory apparatuses. A portable module provides greater flexibility in the use of a laboratory apparatus.

The data processing device preferably comprises a computing unit, in particular a CPU, further preferably at least one data storage device, in particular for volatile and/or permanent storage of data. The data processing device is preferably configured for establishing—by means of the first interface device—one or several first data connections having one or several user interface devices, which may in particular be components of the laboratory apparatus; preferably establishing via the second interface device a second data connection with the laboratory apparatus.

An interface device serves as a connection of two devices, which each are able to process—in particular are able to send and/or receive—signals, in particular information, in particular data. An interface device may include at least one hardware interface and/or at least one software interface.

Hardware interfaces are particularly interfaces arranged between electrically operating units, according to the common understanding in electrical engineering and electronics. In this context, the term "hardware interface" in particular also refers to the connection components between at least two electrically operating units by oneself, thus in particular to all the components that enable this connection, e.g. integrated circuits, electronics and wires, by means of which electrical signals are sent between the at least two electrically operating units. These two electrically operating units may in particular a laboratory apparatus and an external data processing device, or two laboratory apparatuses, or two electrically operating units within one laboratory apparatus. A hardware interface does not need, but may comprise a detachable connection device for releasing and/or recovering a connection, in particular by means of at least one plug.

Software interfaces, in particular data interfaces from the software side, are particularly logical points of contact in an information management system, in particular software system: they enable and control the exchange of commands and data between different processes and components. Software interfaces can only be data-oriented interfaces used for communication. In this case, the software interface only comprises the information that is exchanged between system components to be involved.

The term "device-controlled handling" means that the handling of at least one laboratory sample is at least partially controlled, in particular performed, by the laboratory apparatus. As far as the handling is controlled and/or performed by the laboratory apparatus, this is in particular in so far not controlled and/or carried out by the user, in particular not manually controlled and/or carried out by the user.

Under a device-controlled handling is preferably further understood that the handling is at least partially controlled, in particular carried out, by the laboratory apparatus depending on the at least one user input. The user input may occur before the handling starts and/or during the handling. The user input preferably occurs via a user interface device, which is preferably a component of the laboratory apparatus, or is provided separately from the laboratory apparatus and is signal-connected to the control device of the laboratory apparatus. The user input in particular serves for inputting of at least one parameter, whose value affects and/or controls the handling. This parameter may in particular be a program parameter.

The "device-controlled handling" in particular designates the at least partially automated handling. In a partially automated handling, it is in particular feasible that the handling is carried out so that after starting the handling and before finishing the handling at least one user input occurs, with which the user can influence the ongoing handling, in particular by e.g. answering—in particular confirming or denying an input or carrying out other inputs—an automated request, which occurs by means of a user interface device of the laboratory apparatus. In the partially automated handling, it is in particular possible that the handling comprises several handling steps, which are—in particular successively in time—carried out automatically, and comprising at least one handling step, which requires an user input, in particular taking place via an user interface device.

A device-controlled handling is preferably a program-controlled handling, thus it is a handling controlled by a program. Under a program-controlled handling of a sample is to be understood that the procedure of the handling substantially occurs by executing a plurality or multiplicity of program steps. Preferably, the program-controlled handling occurs in use of at least one program parameter, in particular in use of at least one program parameter selected by the user. A user-selected parameter is also referred to as user parameters. The program-controlled handling preferably occurs by means of a digital data processing device, which can in particular be part of the control device of the laboratory apparatus. The data processing device may comprise at least a processor, i.e. a CPU, and/or at least one microprocessor. The program-controlled handling is preferably controlled and/or carried out according to the specifications of a program, in particular a control program. In particular, no user action is substantially required in a program-controlled handling, at least after the detection of program parameters required from the side of a user.

Under a program parameter is understood a variable, which can be set in a predetermined manner within a program or sub-program and is valid for at least one execution (call) of the program or sub-program. The program parameter is defined, e.g. by the user, and controls the program or sub-program and effects a data output depending on this program parameter. In particular, the control of the device—in particular the control of the handling by means of the at least one handling device—is affected and/or controlled by the program parameter and/or is controlled by the data outputted by the program.

A program parameter can be a user-required program parameter. A user-required program parameter is characterized by the fact that it is essential for the execution of a handling, in particular for the execution of a method program. Other program parameters that are not user-required can be derived from the user-required program parameters or can made available in another way, in particular optionally can be set by the user. The setting of a program parameter by a user in particular occurs by displaying a selection of potential, predefined values from a list of predefined values stored in the laboratory apparatus, wherein the user selects—and thus sets—the desired parameter from said list. It is also possible that this program parameter is set by inputting the value by the user by e.g. inputting a number by means of a keypad, wherein said number corresponds to the desired value, or by increasing or rather decreasing a value continuously or incrementally by the user, until this value corresponds to the desired value, and therefore sets the values. Other forms of input, e.g. by voice control and/or gesture control, are possible.

Under a program is in particular meant a computer program. A program is a sequence of instructions, in particular consisting of declarations and instructions, in order to be able to process and/or solve a specific function, task or problem using a digital data processing system. A program is usually present as software that is used with a digital data processing system. The program can in particular be present as a firmware, in particular in the case of the present invention as firmware of the control device of the laboratory apparatus. The program is usually present on a disk as an executable program file, frequently in the so-called machine code, which is loaded for execution in the computer's working storage, wherein the computer refers to the digital data processing system. The program is processed and thus executed as a sequence of machine commands, i.e. processing unit commands by the processing unit/units of the computer. In particular, "computer program" also means the source code of the program, from which the executable code may arise during the process of controlling the laboratory apparatus.

As an instruction, a key element of a programming language is commonly referred to. The programs of such languages primarily compose of one or more instructions. An instruction is a regulation formulated in the syntax of a programming language, which is to be executed within the scope of the eradication of the program. The way an instruction is syntactically configured is defined by the particular programming language or rather its specification. In the machine-level programming, instructions are often referred to as a command. Instructions are usually assignments, control instructions (such as jumps, loops and conditional instructions) and procedure calls. Partially and depending on the programming language, representations, declarations, class and function definitions may also be instructions. The instructions of the control program can be configured in the common way.

As is conventional, a program module is understood to be a complete functional unit of software, consisting of a sequence of processing steps and data structures. Here, in particular, the following definitions may apply: the content of a module is often a recurring calculation or a handling of data, which needs to be carried out a number of times. Modules offer an encapsulation by separating interface and implementation: the interface of a module defines the data elements which, as input and result of the processing, are required by the module. The implementation contains the actual program code. By way of example, a module is called as a function or sub-program, executes a number of processing steps and, as a result, provides data back to the calling program. A module itself is able to call further modules—thus, a hierarchy of program calls is possible. The data structures and processes set in modules can, when necessary, be inherited and inherited by other modules. Therefore, modules are an essential element in structured and object-oriented programming.

A control program is understood to mean an executable computer program, which preferably controls and/or performs the desired handling of the at least one sample, in particular as a function of at least one program parameter. This program parameter can be a program parameter influenced and/or set by the user. In particular, the handling can be controlled by virtue of the control device generating one or more control parameters as a function of the program parameters, wherein, by means of the control parameters, the at least one handling device is controlled. The laboratory apparatus preferably has an operating system, which can be or comprise a control program. In particular, the control program can denote an operating system of the laboratory apparatus or a component of the operating system. The operating system controls the handling and further operating functions of the laboratory apparatus.

In particular, the control program can be signal connected to the user interface device and/or can control the user interface device. The control device of the user interface device can be integrated into the control device of the laboratory apparatus or can be embodied separately from this control device. The control device of the user interface device can be integrated in the control of the laboratory apparatus, can be controllable by the control program and/or can in particular be integrated into the control program. The control program can control further preferably provided functions of the laboratory apparatus, for example an energy-saving function of the laboratory apparatus or a communication function for communication with external data processing devices, which are in particular provided separately from the laboratory apparatus and are in particular not provided to be a component of the laboratory apparatus.

A method program is understood to mean a program, which determines the specific progress of a handling, in particular in accordance with a predetermined type of handling and/or in accordance with a manner set from the side of the user.

The term laboratory apparatus is in particular referred to a device that is configured for device-controlled handling of at least one laboratory sample and is configured for use in a laboratory. In this laboratory, it may in particular be a chemical, biological, biochemical, medical or forensic laboratory. Such laboratories serve the research and/or the analysis of laboratory samples, but may also serve the production of products by means of laboratory samples or may also serve the production of laboratory samples.

A laboratory apparatus is preferably one of the following laboratory apparatuses and/or is preferably configured as at least one of the following laboratory apparatuses: a laboratory centrifuge, also referred to as "centrifuge" within the scope of the description of the present invention; a thermal cycler, also referred to as "cycler" within the scope of the description of the present invention; a laboratory spectral photometer, also referred to as "bio-spectrometer" within the scope of the description of the present invention; a cell counting assembly, also referred to as "cell counter" within the scope of the description of the present invention, in particular optical counting assemblies; a laboratory incubator, also referred to as "incubator" within the scope of the description of the present invention; a laboratory shaking device, also referred to as "shaker" within the scope of the description of the present invention; a laboratory mixing device, also referred to as "mixing device"; a laboratory freezing device, also referred to as "freezer" within the scope of the description of the present invention; a bioreactor, also referred to as fermenter within the scope of the description of the present invention; a safety workbench, in particular biological safety workbench, also referred to as "biosafety cabinet" within the scope of the description of the present invention; a sample plate reading device, also referred to as "plate reader" within the scope of the description of the present invention, in particular "microplate reader"; a laboratory machine for the handling of fluid samples, in particular a pipetting machine.

A laboratory centrifuge is a device, which operates using inertia. The laboratory centrifuge, in particular the handling device of the laboratory centrifuge, in particular comprises at least one rotor, in which the at least one laboratory sample can be arranged. The at least one rotor is arranged in a rotatable manner in at least one centrifuge chamber. The laboratory centrifuge, in particular the handling device of the laboratory centrifuge, comprises at least one drive device, by means of which the rotation is driven and/or braked. The samples can be arranged in the at least one rotor, preferably in laboratory containers, e.g. sample tubes, which are arranged in appropriate holders in the rotor. The laboratory centrifuge, in particular the handling device of the laboratory centrifuge, preferably comprises at least one heating/cooling device, by means of which the temperature of the at least one sample arranged in the rotor can be controlled and/or regulated. The laboratory centrifuge, in particular the handling device of the laboratory centrifuge, preferably comprises a timer device, by means of which time parameters of the rotation or temperature setting can be controlled. The functionality is based on the centrifugal force, which occurs due to a uniform circular movement of the samples to be centrifuged. The centrifugal force is used for the substance separation of substances having different densities, which are contained within a sample. A centrifuge may perform a separation process, in which in particular the components of suspensions, emulsions and/or gas mixtures are separated. The device-controlled handling of the at least one laboratory sample corresponds to a rotation handling in a laboratory centrifuge with at least one sample, wherein said sample is subjected to said rotation handling. Potential parameters, in particular program parameters, in particular user parameters, which are used for the influence of a rotation handling, in particular define a temperature of the laboratory centrifuge, a rotation speed of the laboratory centrifuge, a time parameter of the rotation or a temperature setting, and/or at least one procedure parameter, which affects or defines the procedure, in particular the sequence, of a rotation program comprising several rotation steps. The temperature of the laboratory centrifuge may in particular be at least a temperature within the at least one rotor, in particular at least one temperature of at least one sample.

A thermal cycler is a device that is able to set successively in time the temperature of at least one sample to a predetermined temperature and to keep said sample at this temperature level for a predetermined interval. The procedure of this temperature control is cyclical. That means a predetermined temperature cycle, i.e. a sequence of at least two temperature levels, is performed repeatedly. This method in particular serves for the performance of a polymerase chain reaction (PCR). In this context, a thermal cycler is sometimes also referred to as a PCR block. A thermal cycler, in particular the handling device of the thermal cycler, preferably has a thermal block 33, 408 (cf. FIG. 1, 3). A thermal block is a sample holder made of a heat-conducting material, mostly a metal-containing material or a metal, in particular aluminum or silver. The sample holder comprises a contacting side, which is contacted by at least one heating/cooling device of the thermal cycler, in particular by a Peltier element. The thermal cycler, in particular the handling device of the thermal cycler, comprises a control device with at least one control loop, to which the at least one heating/cooling device is assigned as an actuator and at least one temperature measurement device is assigned as a measurement element. The temperature is controlled to a temperature level by means of the control system. A cooling element of the thermal cycler, in particular of the handling device of the thermal cycler, serves for cooling sections of the thermal cycler, in particular for cooling the Peltier elements. The thermal cycler, in particular the handling device of the thermal cycler, may comprise further heating and/or cooling elements. The thermal cycler, in particular the handling device of the thermal cycler, preferably comprises a timer device, by means of which time parameters for setting the temperature cycle can be controlled. The device-controlled handling of the at least one laboratory sample corresponds to a temperature cycle handling in a thermal cycler, to which the at least one sample is subjected. Potential parameters, in particular program parameters, in particular user parameters, which are used to influence a temperature cycle handling, in particular define the temperature of a temperature level, the duration of a temperature level, the control of further heating and/or cooling elements and/or the number of temperature levels or cycles and/or at least one procedure parameter, which influences or defines the procedure, in particular the sequence, of a temperature control program consisting several steps.

A laboratory spectral photometer is a device, which, by illuminating at least one measurement volume of at least one laboratory sample, mostly over the entire spectrum of visible light from infrared to ultraviolet, investigates the remission values. Remission refers to the situation that a measurement volume absorbs a portion of the light spectrum and transmits (transparent media) or rather reflects (opaque media) another portion of the spectrum. The laboratory spectral photometer is in particular used to measure the absorptivity of a sample depending on the light wavelength. Moreover, it is in particular possible to extend the field of application of the laboratory spectral photometer by means of different modules. By way of example, it is conceivable to arrange a fluorescence module for measuring fluorescence or a tempering module for tempering the sample in the spectrometer. The measured absorption spectrum in particular comprises the light intensities measured at specific wavelengths. The absorption spectrum is characteristic for the laboratory sample and the substance contained therein or the substances, respectively. This can be used for qualitative analysis of the laboratory sample. If the liquid sample or rather the substance dissolved therein is known, the concentration of the dissolved substance can be investigated by measuring the absorption. This can be used for quantitative analysis of the laboratory sample. The laboratory spectral photometer, in particular the handling device of the laboratory spectral photometer, preferably comprises at least one light source, preferably at least one timer device, preferably at least one photodetector. The device-controlled handling of the at least one laboratory sample corresponds to a light and measurement handling in a laboratory spectral photometer, to which the at least one sample is subjected. Potential parameters, in particular program parameters, in particular user parameters, which are used to influence a light and measurement handling, in particular define the optical light spectrum, by means of which the at least one sample is irradiated and/or at least one procedure parameter, which influences or defines the procedure, in particular the sequence, of a light and measurement handling program consisting of several steps.

A cell counting assembly serves for counting biological cells or rather particles, which are contained within a laboratory sample. There are different physical principles, which are considered for counting cells, in particular optical methods, in which the laboratory sample to be measured is arranged in a counting chamber, particularly in the case of automatically operating assemblies, additional illumination occurs and an image of the cells or rather particles arranged in the counting chamber is acquired and evaluated. A further well-established method is the impedance measurement: a cell counting assembly embodied as a Coulter counter directs the laboratory sample comprising the cells through an aperture ("measurement port"). Each passage of a cell through the aperture is detected electrically as a countable event. Optical cell counting assemblies, in particular the handling device of the cell counting assembly, preferably comprise, depending on the embodiment, at least one light source, at least one image acquisition unit and at least one image evaluation unit, and additionally, inter alia, a positioning device. The device-controlled handling of the at least one laboratory sample corresponds e.g. to a light and measurement handling in the case of an optical cell counting assembly, a pumping and measurement handling in the case of a device, which operates according to the Coulter principle, to which the at least one sample is subjected. Potential parameters, in particular program parameters, in particular user parameters, which are used to influence a light and measurement handling or the pumping and measurement handling, in particular define the light intensity of the light source, by means of which the at least one sample is irradiated and/or at least one procedure parameter, which influences or defines the procedure, in particular the sequence, of a light and measurement handling program or a pumping and measurement handling program consisting of several steps. Besides, in the case of optical counting assemblies, the algorithms necessary for the image evaluation, and the sequence and parameterization thereof are decisive for the significance of the measurement result. Optical measurement devices, but also Coulter counters, often use counting chambers for single use ("consumables"); these are plastic articles in the style of conventional Neubauer counting chambers or rather, in the case of Coulter counters, "lab-on-a-chip"-like disposable counting chambers. However, there are also devices, which operate without these consumables (e.g. "CASY").

A laboratory incubator is a device by means of which controlled climatic conditions for various biological development and growth processes can be created and maintained. It serves for the creation and maintenance of a microclimate having regulated gas and/or humidity and/or temperature conditions in an incubator chamber, wherein this handling may be dependent on time. The laboratory incubator, in particular the handling device of the laboratory incubator, may in particular comprise a timer device, in particular a timer switch, a heating/cooling apparatus and preferably a setting for the control of the substitute gas supplied to the incubator chamber, in particular fresh air, a setting device for the composition of the gas in the incubator chamber of the laboratory incubator, in particular for setting the $CO_2$ and/or $O_2$ content of the gas and/or a setting device for setting the humidity in the incubator chamber of the laboratory incubator. The laboratory incubator, in particular the handling device of the laboratory incubator, in particular comprises the incubator chamber, further preferably a control device having at least one control loop, to which at least one heating/cooling device is assigned as an actuator and at least one temperature measurement apparatus is assigned as a measurement element. The temperature can be controlled in the incubator by means of the control device. $CO_2$ incubators in particular serve for cultivating animal or rather human cells. Incubators may comprise turning apparatuses for turning the at least one laboratory sample and/or a shaker device for shaking or rather moving the at least one laboratory sample. The device-controlled handling of the at least one laboratory sample corresponds to a climate handling in a laboratory incubator, to which the at least one sample is subjected. Potential parameters, in particular program parameters, in particular user parameters, which are used to the influence of a climate handling, in particular define the temperature of the incubator chamber, in which the at least one sample is incubated, the $O_2$ and/or $CO_2$ partial pressure in the incubator interior, the humidity in the incubator interior and/or at least one procedure parameter, which influences or defines the procedure, in particular the sequence, of an incubation handling program consisting of several steps.

A laboratory shaking device serves for the movement of a laboratory sample, in particular for mixing a laboratory sample comprising a multiplicity of components. There are different embodiments of laboratory shaking devices, in particular overhead shaking devices or flatbed shaking devices. Laboratory shaking devices can comprise a tempering function for tempering the at least one laboratory sample, and can particularly comprise an incubator function for incubating the at least one laboratory sample in controlled climatic conditions. Laboratory shaking devices, in particular the handling devices thereof, can in particular be arranged for performing an oscillating movement. Laboratory shaking devices, in particular the handling device thereof, in particular comprise a drive for driving the movement, in particular comprise a timer device, by means of which time parameters of the setting of the shaker handling can be controlled, and particularly comprise at least one heating/cooling device and at least one control device with at least one control loop, which is assigned the at least one heating/cooling apparatus as actuator and at least one temperature measurement apparatus as measurement element. The device-controlled handling of the at least one laboratory sample corresponds to a shaker handling in a laboratory shaking device, to which the at least one sample is subjected. Potential parameters, in particular program parameters, in particular user parameters, which are used for the influence of a shaking handling, particularly define the movement intensity, in particular the movement frequency in an oscillating drive, a time period in the shaking handling and/or at least one procedure parameter, which influences or defines the procedure, in particular the sequence, of a shaker handling program consisting of several steps.

A laboratory mixing device also referred to as "mixing device", serves—like the laboratory shaking device—for the movement of a laboratory sample, in particular for mixing a laboratory sample comprising several components. In comparison to a laboratory shaking device, a laboratory mixing device enables movements having higher frequencies, in particular having higher rotation speed values. Laboratory mixing devices, in particular the handling devices thereof, can particularly be arranged for performing an oscillating movement. Laboratory mixing devices, in particular the handling devices thereof, particularly comprise a drive for driving the movement, particularly comprise a timer device, by means of which time parameters of the setting of the mixer handling can be controlled and particularly comprise at least one heating/cooling device and at least one control device with at least one control loop, which is assigned the at least one heating/cooling device as actuator and at least one temperature measurement device as measurement element. The device-controlled handling of the at least one laboratory sample corresponds to a mixer handling in a laboratory mixing device, to which the at least one sample is subjected. Potential parameters, in particular program parameters, in particular user parameters, which are used to influence a mixer handling, particularly define the movement intensity, in particular the movement frequency in an oscillating drive, a time period in the mixer handling and/or at least one procedure parameter, which influences or defines the progress, in particular the sequence, of a mixer handling program consisting of several steps.

A laboratory freezing device serves for the storage of at least one laboratory sample in a freezer room at controlled temperatures, in particular in the freezer range from −18° C. to −50° C. or in the ultra-freezer range from −50° C. to −90° C. In particular, a laboratory freezing device is not a refrigerator, which can be in particular used for cooling at temperatures in the range from 0° C. to 10° C. or from −10° to 10° C. A laboratory freezing device, in particular the handling device of the laboratory freezing device, particularly comprises at least one cooling device and at least one control device having at least one control loop, to which at least one cooling device is assigned as an actuator and at least one temperature measurement device is assigned as a measurement element. A laboratory freezing device, in particular the handling device of the laboratory freezing device, particularly comprises a control measurement device for measuring the temperature and/or in particular at least one alarm device, by means of which an alarm signal is emitted, if the temperature measured in the freezer space leaves a permitted temperature range. A laboratory freezing device, in particular the handling device of the laboratory freezing device, can particularly comprise an information reading device for reading information. This information can be contained in an information medium, which can be connected to an article. This article can in particular be a sample container, which can contain at least one laboratory sample. The information medium can in particular comprise an RFID chip or other identification features, such as e.g. a barcode, a data matrix code, a QR code, which can be read by appropriate methods. The device-controlled handling of the at least one laboratory sample corresponds to a low-temperature handling in a laboratory freezing device, to which the at least one sample is subjected. Potential parameters, in particular program parameters, in particular user parameters, which are used to influence a low-temperature handling, particularly define the temperature of the freezer room, in which the at least one sample is frozen and/or the information reading procedure, which is preferably performed, when an article provided with an information medium is transferred from a user into the laboratory freezing device.

A bioreactor comprises a container, in which specific microorganisms, cells, algae, plants (e.g. mosses) are cultivated (also: fermented) under conditions, which are as ideal as possible. The operation of a bioreactor is therefore an application of biotechnology, which uses biological processes, in particular bioconversion or biocatalysis, in technical devices or rather makes them available. Factors, which can be controlled or monitored in most bioreactors, in particular by setting appropriate parameters, are the composition of the nutrient solution, the oxygen supply, temperature, pH, sterility and/or other factors. The purpose of cultivation in a bioreactor may be the acquisition of cells or constituents of cells, or the acquisition of metabolic products. By way of example, these can be used as an active ingredient in the pharmaceutical industry or as a basic chemical in the chemical industry.

The decomposition of chemical compounds may also take place in bioreactors, such as e.g. in sewage water handling in sewage works. The production of beer, wine and other such products likewise occurs in bioreactors. The most diverse types of organisms are cultivated in bioreactors for various purposes. Therefore, a bioreactor can be embodied in different ways. It can be embodied as stirred tank reactor, which may comprise a volume from a few milliliters to hundreds of liters and can be filled with nutrient solution. It can also be used or rather embodied as a fixed bed reactor or photobioreactor. A bioreactor can be part of a bioreactor system, preferably of a parallel bioreactor system. In such a parallel bioreactor system, a multiplicity of bioreactors are operated in parallel and controlled with high precision. A bioreactor, in particular the handling device thereof, particularly comprises a stirring device for stirring the sample contained within the reactor container, in particular for stirring the nutrient solution. A bioreactor, in particular the handling device thereof, in particular comprises a pumping device for pumping the laboratory sample, which is preferably embodied as nutrient solution. A bioreactor, in particular the handling device thereof, in particular comprises a setting device for setting a gas content in the reactor container, in particular the content of $CO_2$ and/or $O_2$ or rather of dissolved oxygen (DO). A bioreactor, in particular the handling device thereof, in particular comprises a setting device for setting, in particular controlling, a pH value in the sample in the reactor container. The device-controlled handling of the at least one laboratory sample in particular corresponds to a nutrient solution handling in a bioreactor, to which the at least one sample, preferably embodied as nutrient solution, is subjected to. Potential parameters, in particular program parameters, in particular user parameters, which are used for the influence of a nutrient solution handling, in particular define the temperature of the nutrient solution in the reactor container and/or the speed of the stirring device, in particular the rotational speed and/or the pumping speed or rather the metering speed and/or a gas content in the nutrient solution, in particular $CO_2$ and/or $O_2$ or rather dissolved oxygen (DO) and/or the pH value of the nutrient solution and/or at least one procedure parameter, which influences or defines the procedure, in particular the sequence, of a nutrient solution handling program consisting of several steps.

A biological safety workbench in particular serves for secure storage or safekeeping of hazardous materials, in particular for fulfilling a biological protection level. In particular, these levels are standardized in the EU Directive 2000/54/EG on the protection of workers from risks related to the handling of biological agents at work and, in Germany, in the German Ordinance on Biological Substances. A biological safety workbench is intended to prevent laboratory samples stored in a biological safety workbench from endangering the surroundings if danger develops. In particular, safety is ensured by virtue of the atmosphere contained in the receiving region of the biological safety workbench being replaced and, in particular, filtered. In this context, this atmosphere is in particular conveyed through the receiving region by a conveying device and moved through a filter, which filters the atmosphere and, in particular, removes hazardous materials. The safety workbench, in particular the handling device thereof, in particular comprises a conveying device for conveying atmospheric gas, in particular comprises a timer device for measuring a filter operation duration and fan operation duration and/or in particular comprises a measurement device for measuring a conveyed amount of atmospheric gas. The device-controlled handling of the at least one laboratory sample in particular corresponds to an atmospheric gas handling for handling the atmospheric gas, in which the at least one sample is stored, in a biological safety workbench. Potential parameters, in particular program parameters, in particular user parameters, which are used to influence an atmospheric gas handling, in particular define the temperature of the atmospheric gas in the receiving region and/or the flow speed of the atmospheric gas conveyed by the conveying device, the amount of air conveyed, the filter operation duration and/or the fan operation duration.

A sample plate reading device, also referred to as "plate reader" or "microplate reader", is a laboratory apparatus for detecting biological, chemical or physical events of samples in microtiter plates. The use of whose is widely spread in research: for active ingredient research, bioassay validation, quality control and manufacturing processes in the pharmaceutical and biotechnological industry and in academic organizations. The sample plate reading device may in particular comprise at least one light source or radiation source, can comprise at least one photodetector, can comprise a temperature control device for the tempering of the samples or rather the sample plates and can comprise a timer. Sample reactions can be tested in the 6-1536 well formats of microtiter plates. The most common format for sample plates, in particular for microtiter plates, which are used in academic research laboratories or in clinical-diagnostic laboratories, is a 96 well plate (an 8 by 12 matrix) having a typical single volume of between 100 and 200 µl per well. Microtiter plates having a higher density (384 or 1536 well microtiter plates) are typically used in screening applications, if the throughput (number of samples to be processed per day) and assay costs per sample become critical parameters, and these have a typical assay volume of between 5 and 50 µl per well. In particular, the handling is an optical measurement of the microtiter plate, in particular the measurement of an absorption, fluorescence intensity, luminescence, time-resolved fluorescence and/or fluorescence polarization. Potential parameters, in particular program parameters, in particular user parameters, which are used for the influence of a measurement, define e.g. the intensity of the light source, the sensitivity of a photodetector, a time duration and/or a temperature.

A laboratory machine for handling fluid samples, in particular a pipette machine, serves for the device-controlled handling of these samples. A laboratory machine can be a laboratory apparatus or comprise at least one laboratory apparatus of the aforementioned type and/or can be embodied for the performance of at least one, several or all of the handlings that can be executed by this aforementioned laboratory apparatus. A laboratory machine comprises the handling device for automatic, program-controlled handling of the at least one laboratory sample, wherein the handling is controlled using several program parameters, which are at least partly selected by the user. In the context, the sample can, for example, be moved and/or transported by the laboratory machine or rather by a handling device of the laboratory machine. The movement may occur by transport in movable sample containers or by guidance through tube systems, capillaries or pipetting tips. In this contact, liquid samples are in particular transported by suction, i.e. by pipetting, or, more generally, by the application of pressure differences. By way of example, a sample can be divided or diluted by a handling of the sample. The ingredients of a sample can be analyzed or one may, e.g. by way of a chemical reaction, produce new ingredients, in particular in use of the sample. In the context of, in particular, processing and analyzing DNA or RNA or the components thereof, laboratory machines aid in obtaining a wealth of information within a suitable period of time or in analyzing plenty of such samples. This handling device of a laboratory machine mostly comprises a working area with workstations, on which samples can be processed or stored in various ways. For the purposes of transport of e.g. liquid samples between various positions, in particular sample containers, the handling device mostly comprises a device-controlled movement apparatus and device-controlled fluid-transfer apparatus, which can e.g. comprise a pipetting system. Both the transport of the samples and the handling thereof at the various stations can be performed in device-controlled manner, in particular in a program-controlled manner. Then, the handling preferably occurs at least partly or completely automated.

The user of the laboratory machine can preferably define the type of handling for the sample. Such a handling type may, in particular, serve for:
the purification of nucleic acids, in particular:
"MagSep Blood gDNA": purification of genomic DNA from whole blood, in particular using the Eppendorf MagSep Blood gDNA kit;
"MagSep Tissue gDNA": purification of genomic DNA from living tissue, in particular using the Eppendorf MagSep Tissue gDNA kit;
"MagSep Viral DANN/RNA": purification of viral RNA or DNA from cell-free bodily fluids, in particular using the Eppendorf MagSep Viral DNA/RNA kit;
and PCR applications, in particular:
"Compose Mastermix";
"Normalize Concentrations";
"Create Dilution Series";
"Setup Reactions".

A laboratory apparatus, in particular the laboratory machine, is preferably embodied in such a way that the handling of the at least one laboratory sample may occur automatically using the acquired program parameters. A laboratory apparatus, in particular the laboratory machine, in particular the control program thereof, is preferably embodied in such a way that the inputs conducted by the user, in particular the at least one value of at least one program parameter, can be used where necessary, in order to automatically establish further, required program parameters, in particular by the calculation or comparison with data in a database of the laboratory apparatus. In particular, the control parameters preferably used for performing the handling in detail are preferably determined automatically.

As a result of these actions, the operation of the laboratory apparatus becomes more convenient, the user in particular saves designing a program code, since these steps are in particular automatically performed by the laboratory apparatus. In a preferred embodiment of the invention, all that is required from the user are the inputs, which are directly related to the handling of the samples to be performed. Often, these are the same specifications that would also be necessary for performing the handling manually and that are known to the user. By contrast, the parameters, which relate to the control of the laboratory apparatus, in particular the control parameters, do not need to be defined in detail, since these are preferably defined automatically. Control parameters are the parameters required in detail for controlling the technical components of the handling device. Control parameters can be program parameters or can be parameters derived therefrom for the technical implementation, in particular automatically defined parameters.

Preferably, a laboratory apparatus, in particular the laboratory machine, automatically selects the fitting set of program parameters based on the handling type selected by the user, wherein the program parameters thereof required from the side of the user are then requested from the user in the steps (b) and (c). On the one hand, the set of program parameters can include the program parameters required from the side of the user and on the other hand, can include further program parameters. These further program parameters can be defined automatically depending on the selected type of handling, or can be defined automatically depending on at least one or all program parameters inputted by the user and/or can be stored in the storage device. The stored sets of parameters are preferably optimized for the type of handling—or become optimized by the laboratory machine—such that the user preferably does not require specialist knowledge for optimizing the parameters. The control parameters, which are necessary for performing the specific handling by means of the handling device, are derived from the set of program parameters.

A program parameter set of program parameters specific to a handling type is preferably defined for this handling type. The program parameters of this set of program parameters can in particular define the accessories to be used for the handling, e.g. sample container, transport container and/or tools to be used and/or further consumables.

The correlation between the set of program parameters and the type of handling is stored in the storage device of the laboratory apparatus, in particular of the laboratory machine. Preferably the laboratory machine is embodied in such a way that the user can store and/or use more such correlations in the laboratory apparatus. The operation of the laboratory machine becomes particularly efficient by these correlations in combination with the clear and well-structured request of the program parameters. This correlation preferably occurs using one or more program modules, wherein in each case a program module is respectively tailored to a specific application:

Preferably, the laboratory machine comprises at least one program module, wherein a predetermined program module serves for the control of a predetermined laboratory task for handling of laboratory samples.

Preferably, the at least one program parameter, in particular the program parameter required from the side of the user, is selected from the following quantity of physical values, which are relevant for a laboratory sample by means of the handling device: number of samples, dilution factor, target volume, position of the samples in a sample vessel holder or in a microtiter plate, sample temperature, points of time and/or time differences, temperatures or differences in temperature, rates of change of such parameters, etc.

Preferably, the control program comprises instructions for executing the following step, in particular the control device is arranged for performing the following steps of the laboratory apparatus:

Creating a method program using the program parameters inputted by the user, and storing the method program in a storage device, wherein the storage program is editable by the user. That way, the use of the laboratory apparatus, in particular of the laboratory machine, is more flexible.

The laboratory machine may be modified so that further types of handling may be performed. This may occur in that the data and/or programs or program components, which are essential in this context, in particular a program module assigned to the type of handling, are transferred subsequently to the laboratory machine, in particular to its storage device.

A laboratory sample is a sample that can be handled in a laboratory. Instead of the term laboratory sample, also the term "sample" is used in the description of the invention. The sample can be a fluid. The sample can be liquid, jellylike, in powder form or a solid state body or comprising such phases. The sample may be a mixture of such phases, in particular a liquid mixture, a solution, a suspension, e.g. a cell suspension, an emulsion or dispersion. A solution is a homogeneous mixture comprising at least two substances. A liquid sample may be one, which is usually handled in a biological, chemical, medical laboratory. A liquid sample can be an analysis sample, a reagent, a medium, a buffer, etc. A solution comprises one or more dissolved solid, liquid or gaseous substances (solutes), and further comprises a preferably liquid solvent (solvent), which in particular forms the larger portion or largest portion of the volume forming the solution. The solvent itself may be a solution.

The handling of a laboratory sample(s) may comprise one or more of the following procedures, in particular simultaneously or successively:

Transport of the laboratory sample, in particular by a transport device, under the action of gravity and/or a force, which is effected by the laboratory machine;

Contactless (non-invasive) physical handling of the sample, in particular thermal handling, in particular heating and/or cooling, in particular controlled tempering of the sample; or freezing or defrosting the sample, or other thermal induction of a phase change of the sample, e.g. evaporating, condensing, etc.; magnetic handling of the sample; optical handling of the sample, in particular irradiating the sample with radiation, in particular light, in particular visible light, infrared light or UV light, or the detection of such radiation, in particular fluorescent light from said sample; magnetic handling of a sample having magnetic components, in particular magnetic separation of magnetic components, in particular "magnetic beads", of a fluid phase of the sample; moving the sample, thus performing a mechanical handling of the sample, in particular shake, rotate, oscillate, vibrate, centrifuge, acoustic handling, in particular with ultrasound, each e.g. for the purpose of mixing the sample or for separating of components within the sample or for transporting the magnetic components out of the sample or into the sample;

Invasive physical handling of the sample, thus performing a mechanical handling of the sample: introducing of stirring tools, e.g. stirring rod or magnetic stir bar into the sample and stirring, introducing a probe for acoustic or ultrasound handling, introducing means of transport, in particular transport containers in the sample, e.g. dispenser tip or pipette tip or hollow needle or tube; addition of other additives in the sample;

Chemical, biochemical or biomedical handling of the sample: adding chemical (e.g. reactant, reagent, solvent, solute), biochemical (e.g. biochemical macromolecules, e.g. DNA, DNA constituents, pharmaceutical agents) or biomedical (blood, serum, cell medium) substances;

Storage of the sample, in particular for a programmatically defined period of time, especially under specific physical conditions, e.g. at a specific temperature, temperatures, or temperature changes, in particular repeated temperature changes, e.g. cyclic and/or periodically repeated temperature changes, and/or setting an ambient pressure, e.g. applying an overpressure or an underpressure, in particular a vacuum, and/or adjusting a defined ambient atmosphere, e.g. an protective gas or a certain humidity, under specific radiation conditions, e.g. shielded from visible light in the dark or under a defined irradiation;

Measurement or analysis of the sample, and in particular analysis by a non-invasive and/or invasive handling of the sample, in particular in order to measure at least one or several chemical, physical, biochemical and/or medical properties of the sample; in particular counting cells using Cell-counter;

Processing the sample, in particular changes of at least one property of the sample, in particular by non-invasive and/or invasive handling of the sample.

This handling particularly occurs program-controlled, using at least one program parameter.

In particular, this handling occurs according to at least one control parameter, which determines the handling of the laboratory sample by means of the handling device. A control parameter can define a period of time, a point in time, a specific sample volume and/or metering volume, a specific sample temperature, etc. A control parameter can relate to the automatic use of a specific transport head, a specific type of a transport container, a specific type of a sample container, one or more individual samples or of specific positions of these components in the working area. A control parameter can relate to the handling of an individual sample or the handling of several or a multiplicity of samples.

A control parameter is preferably selected automatically by the laboratory apparatus, in particular the laboratory machine, in particular is selected automatically depending on at least one program parameter, which is selected by the user. As a result, an advantage for the user is that he does not need to determine all control parameters individually. The user does not need to have knowledge about the programming of the laboratory apparatus. Rather, the control parameters required for the handling are selected by means of the program parameters inputted by the user. As a result, the use of the laboratory apparatus is particularly convenient.

A control parameter can also correspond to a program parameter.

The transport of a sample may be a transport from a sample container into a transport container and/or from the transport container into a sample container or any other target location. This transport in particular occurs program-controlled, using at least one program parameter.

The transport container can be e.g. a dispenser container, which comprises a movable plunger and an inlet/outlet opening. The plunger generates underpressure or rather overpressure in the dispenser container and thus sucks the sample into the container or releases the sample again. This procedure follows the displacement principle, i.e. the sample to be moved, which is usually liquid and therefore incompressible, is subjected to forced movement by virtue of the volume previously taken up by the sample being moved by the plunger. In general, this plunger is moved, in particular moved under program control using a movement device, which is assigned to the laboratory machine.

The transport container can further be a pipette tip. A pipette tip has an inlet/outlet opening and a second opening. The second opening is coupled to a suction device, such that a liquid sample can be sucked (pipetted) from a sample container into the transport container by means of underpressure. The sample is released by ventilating the suction region, by means of gravity and/or overpressure, which e.g. is generated in the pipette tip by means of the second opening.

The transport container preferably consists partly or entirely of plastic. It is preferably a consumable article, which is typically only used for one handling or a small number of handling steps of the sample. However, the transport container can also consist partly or entirely of another material.

The transport of a sample can be a transport of the sample from an initial position to a target position. The initial position may be present, if the sample is arranged in a first sample container and the target position of this sample can be the position thereof in a second sample container, into which the sample is transferred. In this context, this type of transport is also referred to as sample transfer or transfer. In practice, a sample transfer is mostly performed in order to transfer a sample from a storage container, in which e.g. the sample was stored and/or which may e.g. contain a relatively large amount of the sample, into a second sample container, in which the sample is subjected to further handling. This transport in particular occurs program-controlled, using at least one program parameter.

The transport container preferably is or can be connected to a transport device of the laboratory machine.

A sample container can be an individual container, in which only a single sample is contained, or it can be a multiple container, in which a several individual containers connected to one another are arranged.

A single container can be an open container or a sealable container. In the case of a sealable container, provision can be made for a covering element, in particular a sealing cap. The covering element can be securely connected with the container, e.g. as a hinged cover or hinged closure cap, or can be used as separate component.

In a multiple container, the several single containers are preferably arranged in a fixed position with respect to one another, in particular arranged in accordance with the crossing points of a grid pattern. This simplifies the automated drive to the positions and, in particular, the individual addressing of samples. A multiple container can be embodied as plate element, in which the individual containers are connected in such a way that they form a plate-shaped arrangement. The individual containers can be embodied as recesses in a plate or can be interconnected by bar elements. The plate element may comprise a frame element, in which the single containers are held. These connections of components can be integral connections, i.e. cohesive connections and/or connections generated by a common injection molding process, or they can be generated in a force-fit and/or form-fit manner. In particular, the plate element can be a microtiter plate.

Multiple containers can comprise a plurality (2 to 10) of single containers. They can further comprise a multiplicity (more than 10) thereof, typically 12, 16, 24, 32, 48, 64, 96, 384, 1536 single containers. In particular, the multiple containers can be a microtiter plate. A microtiter plate can be embodied according to one or more industrial standard(s), in particular the industrial standards ANSI/SBS 1-2004, ANSI/SBS 2-2004, ANSI/SBS 3-2004, ANSI/SBS 4-2004.

The maximum sample volume that can be accommodated by a transport container or sample container typically lies between 0.01 ml and 100 ml, in particular 10-100 µl, 100-500 µl, 0.5-5 ml, 5-25 ml, 25-50 ml, 50-100 ml, depending on the type of the selected transport container or sample vessel.

A sample container—equivalent term used to sample vessel—can comprise an information area, which can comprise information about the sample container or the content thereof. The information area may comprise encoded information, e.g. a barcode or QR code or an RFID chip, or information encoded differently. The information may comprise information for identifying the sample and/or a sample container. The laboratory machine may comprise an information reading device for reading this information and preferably for providing said information to the control device.

The sample container preferably consists partly or entirely of plastic. It is preferably a consumable article, which is typically only used for one handling or a small number of handling steps of the sample. However, the sample container can also consist partly or entirely of a different material.

The sample container can preferably be transported by a transport device of the laboratory machine.

The laboratory apparatus, in particular the laboratory machine, is preferably embodied to handle a multiplicity of samples in succession and/or in parallel. In particular, the laboratory apparatus, in particular the laboratory machine, is preferably embodied to handle, in particular to transport, to empty and/or to fill, a multiplicity of sample vessels, in particular single containers and/or multiple containers, in a program-controlled manner.

Preferably, a laboratory apparatus, in particular the laboratory machine, exactly comprises a working area. Such a laboratory apparatus, in particular a laboratory machine, is compact and can particularly be adapted for use on a laboratory bench, wherein it is then in particular also referred to as a tabletop unit. The table can e.g. be the workbench of a chemical, biochemical and biomedical laboratory. The laboratory apparatus, in particular the laboratory machine, can also be configured for the placement in such a laboratory. A laboratory apparatus, in particular laboratory machine, having a working area may also be configured as an independently operating device of such a laboratory, or can be integrated into a device compound.

The laboratory apparatus, in particular laboratory machine, may be configured as a laboratory line, in which several working areas are arranged next one another in such a way that, by means of transport apparatus, a single, several or a multiplicity of samples can be transported successively and/or in parallel between the working areas. A working area of a laboratory line is preferably configured in such a way that a specific laboratory object, mostly relating to the parallel and/or sequential handling of a multiplicity of samples, is performed. A high work throughput of the laboratory line is achieved as a result of this specialization of each working area. In order to perform such a specific object, provision can be made for only one type of handling of at least one sample or for only a few types of handling, e.g. two to ten handling types, to be performed in each working chamber. A handling device for performing a handling, which is characteristic for a specific laboratory apparatus, as described within the scope of the description of the invention, can be arranged at each workstation. The transport apparatus may comprise a rail system and/or a robotic device for program-controlled moving of samples or rather sample containers.

A laboratory apparatus, in particular a laboratory machine, can be connected or connectable to an LIMS. LIMS is an abbreviation for laboratory information and management system. A LIMS is a software system in a known way, which relates to data processing in an automated or partly automated chemical, physical, biological or medical laboratory. Such data can originate from measurements of the samples and/or can relate to the control of the data processing. A LIMS preferably serves for measurement value acquisition and measurement value evaluation. LIMS is used, in order to increase the work throughput in a laboratory and/or to optimize the efficiency of the handling of laboratory samples.

A tool element can be e.g. a transport head for the fluid transfer, in particular a pipetting head, which may comprise a connection section for the connection of one pipette tip (single channel pipetting head) or for the connection of several pipette tips (multiple channel pipetting head). Liquid can be sucked into the at least one pipette tip, if the latter is connected to the connection section by means of at least one pressure and gas-tight channel connected to the pipetting head. In the laboratory machine, this pipetting is performed, in particular, in a program-controlled manner; in particular, it is influenced by at least one program parameter. The transport head can also be a dispensing head, which comprises at least one movement device for moving a plunger of the dispenser tip. In the laboratory machine, the movement device is moved in a in particular program-controlled manner; in particular, it is influenced by at least one program parameter. The transport head can serve for metering liquid, in particular for metering in different areas; a transport head can be configured for metering a liquid sample having a volume that can be selected from a volume range specific to this transport head: e.g. 1-50 μL or 20-300 μL or 50-1000 μL, ("l" and "L" are each an abbreviation for liter). A transport head can be configured as a single-channel head, in which only one sample is transported, or it can be embodied as a multichannel head, in particular an eight-channel head or a 12-channel head, in which several samples are processed or transported in parallel. Preferably, provision is made for specific transport containers, which can be used depending on the respective type of transport head, in particular in accordance with the corresponding volume range.

A tool element can be e.g. a transport head for transporting objects, e.g. a carrier and/or gripper tool for carrying and/or gripping an object. A carrying tool may comprise a fastening section for detachably fastening the object to the carrying tool, e.g. by a force-fit and/or cohesive and/or magnetic connection between the object and the carrying tool. In this manner, it is possible within the work surface or between a multiplicity of working areas and/or work surfaces.

A tool element can further be a handling unit, e.g. for performing a thermal, acoustic, optical and/or mechanical handling of at least one sample.

The laboratory machine may comprise an information reading device, in order to read information regarding a sample and/or a sample container and/or a handling instruction for this sample and/or this sample container and, preferably, make this available to the control device of the laboratory machine.

The laboratory machine preferably comprises at least one timer device and/or preferably at least one timing device, in order to enable the time-dependent handling of the samples. The time-dependent handling preferably occurs program-controlled, and in particular controlled by at least one program parameter.

In a preferred configuration of the laboratory machine according to the invention, the former is configured, depending on the handling type selected by the user and the program parameters inputted by the user, to automatically select one or more of the following components for use in the program-controlled handling:

at least one appropriate sample container, in particular adapted for accommodating a several samples, which are to be processed together, e.g. which are intended to be mixed or between which a chemical reaction or biochemical, biological or biomedical interaction is intended to occur;

at least one appropriate transport container, in particular a pipette tip and/or a dispenser tip;

at least one appropriate transport head, to which the preferably automatically selected transport container can be connected, at least one appropriate tool element, which serves for the performance of the desired handling.

Preferably, the laboratory machine according to the invention is configured, depending on the handling type selected by the user and the program parameters inputted by the user, to automatically select one or more of the following control parameters for use in the program-controlled handling:

at least one period of time, during which a specific work step of the handling is performed;

at least one sample volume and/or metering volume;

at least one work position of the at least one work surface;

movement parameters for defining the movement procedure of the robotic device of the laboratory machine required for the desired handling of the sample.

Due to the automatic selection of said components and/or the control parameters depending on the at least one program parameter, particularly depending on the at least one program parameter selected by the user, an advantage is arisen for the user in that the he does not need to determine the selection of components and control parameters individually. Rather, the selection of the control parameters, which are necessary for the handling, occurs by means of the program parameters inputted by the user. The user does not need to have any knowledge regarding the programming of the machine. As a result, the use of automated equipment is particularly convenient.

Due to the automatic selection of the said components and/or the control parameters depending on the at least one program parameter, it can be achieved that based on the user information (e.g. to dilute 20 samples), the correct pipetting head is automatically used or rather—more generally—the convenient tool, e.g. the transport head and/or the tool head is used. This means that the user does need to decide regarding the best tool, but he only decides regarding a handling that is to be desired, e.g. nucleic acid purification in a desired manner. The user, e.g. a biologist, a lab technician, a medical-technical assistant only has to make the decisions, which he can easy and quick do due to his qualification, however, he does neither be able mastering an abstract programming language, nor he has to perform more complex calculations.

The handling device of the automatic laboratory machine preferably comprises: preferably at least one working area, preferably at least one transport device, preferably at least one handling unit.

Preferably, the laboratory apparatus, in particular the laboratory machine, has the ability to permanently store the program parameters inputted by the user and later to reload said parameters automatically or triggered by the user. Then, the user may change individual parameters, in order to fully define a type of sample handling. Thus, the ease of use is increased and the error rate is decreased. This is advantageous in the context that laboratory apparatuses may be used particularly efficient for repetitive processes.

The laboratory apparatus according to the invention preferably comprises a communication device for the production of a remote data connection for data exchange with an external device, which also comprises an appropriate communication device for the production of a remote connection regarding data exchange with the laboratory machine.

The laboratory apparatus preferably comprises a user interface device for the manual input of data by an user, and for displaying information, in particular contained within these data information, wherein the user interface device comprises a display device, in particular a display, in particular a touch-screen display.

The laboratory device according to the invention may comprise several handling devices. An user interface device may be associated with or rather assigned to a multiplicity of laboratory devices according to the invention, in particular the device is connected or can be connected with these by means of a second interface device, and in particular by means of a second data connection. In this way, the access of the user to more than one laboratory apparatus or to one laboratory apparatus having more than one handling device can be enabled by means of an user interface device.

The invention further relates to a method for the detection of at least one user input in a laboratory device according to the invention, which is configured according to at least one of the preceding claims, comprising the steps of:
- Detecting at least one user movement on the display area using the sensor device;
- Defining at least one program parameter and/or its value depending on the at least one user movement,
- Displaying a graphical sketch element in the display area that represents the at least one user movement.

Further potential preferred embodiments of the method according to the invention can be derived from the description of the laboratory apparatus according to the invention and can be derived from its preferred embodiments.

Further preferred embodiments of the laboratory apparatus according to the invention as well as of the process according to the invention will become apparent from the following description of the exemplary embodiments in conjunction with the figures and their description. The same components of the exemplary embodiments are substantially characterized by the same reference signs, if that is not otherwise described or if it does not appear different from the context. In the drawings:

FIG. 1 schematically illustrates an exemplary embodiment of the laboratory apparatus according to the invention in an isometric perspective view.

Figure 1:
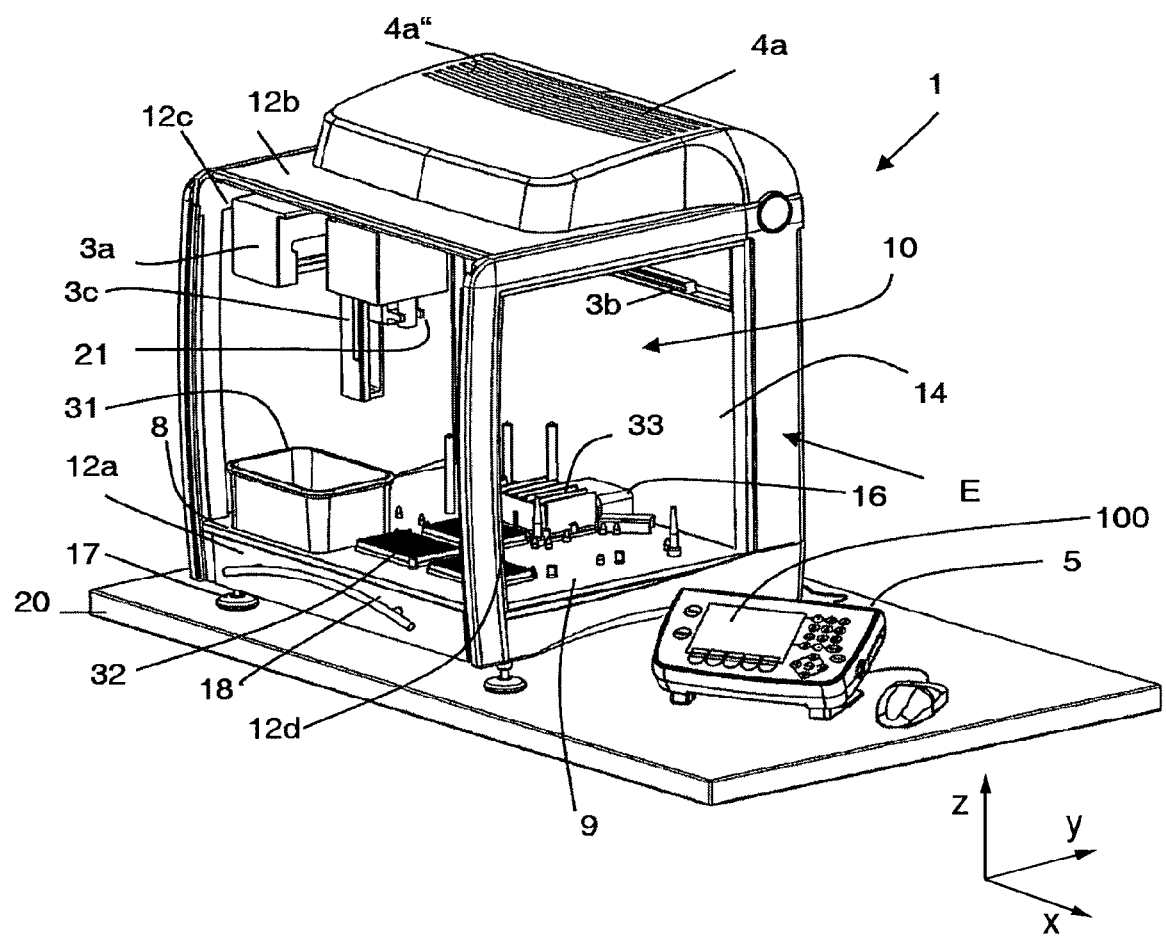

FIG. 1 illustrates the laboratory apparatus 1, which is configured here as a laboratory machine 1 for the handling of fluid samples, namely as a pipetting machine, which comprises in particular an integrated thermal cycler (not shown). The laboratory machine 1 serves the program-controlled handling of these samples.

FIG. 1 illustrates the laboratory machine 1 for the automated processing of liquid samples, in particular for the program-controlled handling of liquid samples. The laboratory machine 1 is a tabletop unit and is arranged with its four sockets 17 on the workbench 20. It disposes of an electronic control device 2 (not shown), which is adapted for processing a program code for the program-controlled handling of the liquid samples. The control device 2 is placed in the control room, which is designated by the arrow E and which is separated from the working chamber 10 by a vertical wall 14. The control room also accommodates the power supply components, which supply the appropriate supply voltage for the electrical components of the laboratory machine.

The laboratory machine 1 comprises a handling chamber 10 for the accommodation of liquid samples to be handled, a program-controlled controllable sample processing device 3 for performing at least one program-controlled handling step of the at least one sample, which is arranged in the processing chamber. The components 3a, 3b, 3c and 3d of the movement device are assigned to the sample processing device 3.

The laboratory machine 1 comprises a housing 12, which comprises a front side 12a, a back side 1f (not shown) arranged opposite to the front side, a top side 12b, a bottom side (not shown) arranged opposite to the top side and lateral sides 12c and 12d arranged opposite to each other. The sides 12a, 12b and 12c are substantially formed of a material, which is transparent to visible light.

Figure 2A:
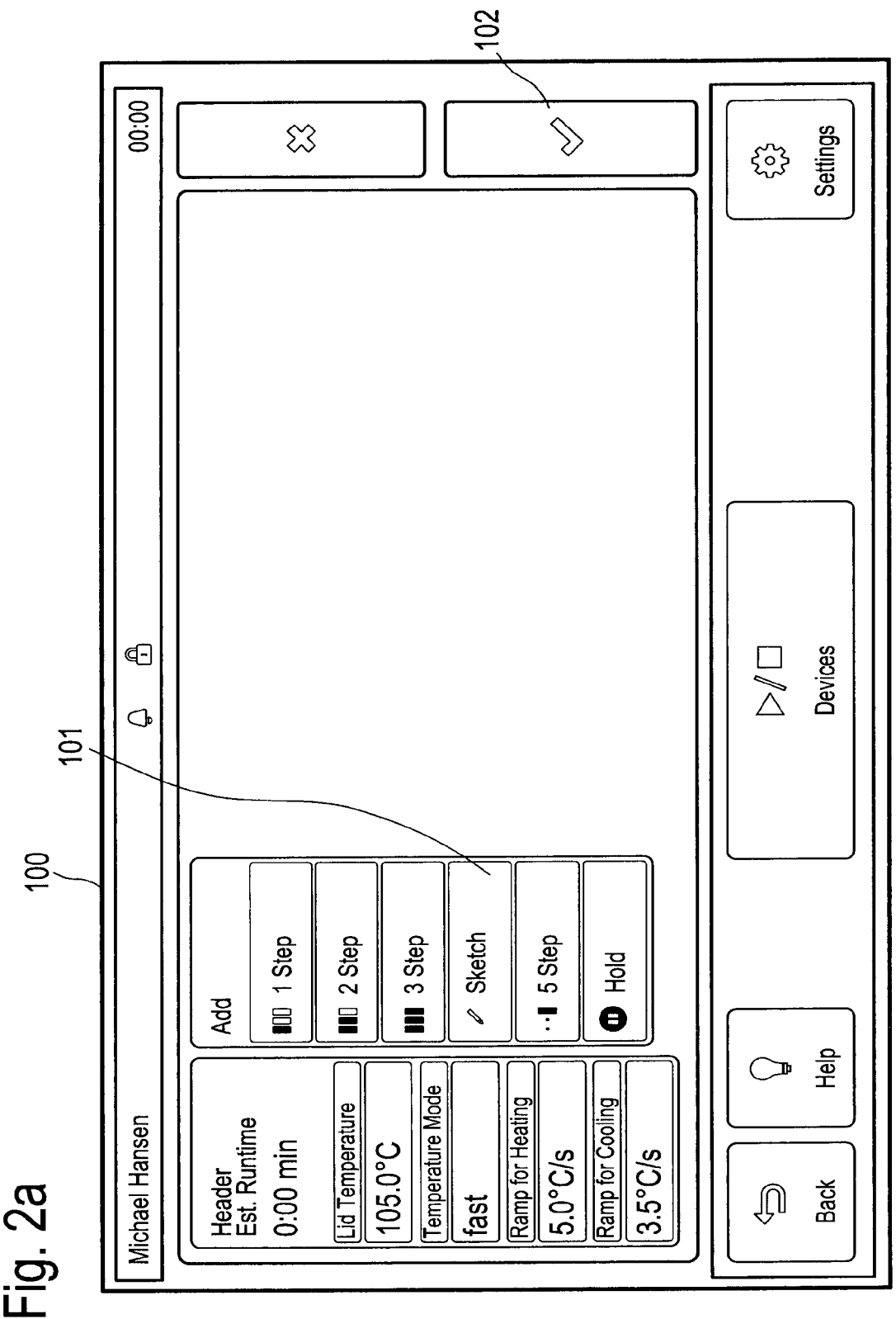
FIG. 2a illustrates the display area of a laboratory apparatus according to a first embodiment of the invention for the provision of a movement detecting input mode.

The front side 12a, which is substantially formed as a door 12a, namely a sliding door 12, can be moved by hand and/or be moved program-controlled and can be closed downwards and substantially along the z-axis of the Cartesian coordinate system. In FIG. 2a the closed position of the door 12a is illustrated.

The handling chamber 10 is limited by the front side 12a and both of the lateral sides 12c and 12d as well as the wall 14 and the work surface 8, which forms the upper side of the bottom plate 9. The work surface 8 provides for six processing stations. The processing stations are substantially planar surfaces in the processing area 8. Pivots serve to align lab ware, say for example thermal rack 33, microtiter plates 32 and waste container 31 at the respective processing station. The accurate positioning enables a precise robot-controlled addressing of the sample container, in particular of the recesses in the microtiter plates 32. A magnetic separator 16 is arranged in the vicinity of the wall 14, where a thermal rack 33, i.e. a temperature-controlled sample vessel holder, is arranged. The magnetic fork (not shown) of the magnetic separator 16 moves from the lateral side into corresponding accommodation channels of the thermal racks, in order to take its magnetic effect laterally at the laboratory vessels (sample tubes).

The laboratory machine 1 comprises two decontamination devices, an electronically controllable air cleaning apparatus for cleaning the air in the handling chamber, which is electronically and digitally controlled by the control device and which comprises a venting apparatus 4a, 4a". The venting apparatus comprises three fans (not shown), which transport a flow of air from outside the apparatus inside the handling chamber.

The control device 2 comprises a control program. The laboratory machine 1 comprises a sample processing device 3, which comprises a movement device having three rail members 3a, 3b, 3c, which correspond to movements along the y, x and z-axis of the Cartesian coordinate system. In order to drive the movement along the desired direction, electronically controllable linear motors are provided. In this way, the mounting head 21 can be moved to any desired position accessible in the processing chamber 10. The movement device is part of a robot system of the sample processing device 3. Together with this, the mounting head 21 is transportable in a programmable manner. Together with the mounting head, a tool device is connectable, e.g. a pipetting head or a gripper. The components arranged in the handling chamber, in particular the sample processing device 3, are part of the handling apparatus of the laboratory machine.

The laboratory machine comprises a user interface device 5, with which an user can do inputs at the laboratory machine. The user interface device 5 comprises at least one display, here exactly one display, which is configured as a touch screen having a display accuracy between 100 dpi and 350 dpi and a spatial resolution of the individual sensors related to the sensor device of the touch screen, which may be equal or lower in comparison to the display resolution of the touch screen. In the touch screen at least one display area, in the present case exactly one display area 100, is arranged, where the user can perform an input on the screen by touching the screen at single points or areas or by performing a curved movement.

In an advantageous movement detecting input mode of the laboratory apparatus, the present invention uses a user movement, by means of which a line-like graphical sketch element is created on the display.

In FIGS. 2a to 2h an user interface is illustrated in each case, which can be displayed in the display area 100 of the laboratory apparatus. The user interface refers to the programming of the thermal cycler integrated in the laboratory apparatus 1 whose temperature-controlled sample accommodation block (tempering block) is integrated to the workstation by the reference sign 33 (FIG. 1).

The user interface illustrated in FIG. 2a enables in the context of the thermal cycler the planning of the tempering process for the samples, which are arranged in the tempering block (or which are still to be transported respectively). In this tempering process, several temperature levels applied for a specific period are repeated cyclically for the duplication of e.g. DNA segments in a PCR sample, wherein in each cycle the number of DNA sequences in the sample is ideally doubled. At least two temperature levels are required per cycle. The change between the temperature levels is carried out at fixed speeds, also referred to as "ramps". These speeds, as well as other program parameters can be set to a default value that can be changed by the user or by an administrator or only by a manufacturer. The movement detecting input mode of the laboratory apparatus according to the invention is activated by the touch of the subarea 101, configured as a virtual input button, of the display area 100, also referred to as "button 101". In another preferred embodiment, the "button 101" is not provided and the movement detecting input mode is activated automatically during the display of this user interface.

Figure 2B:
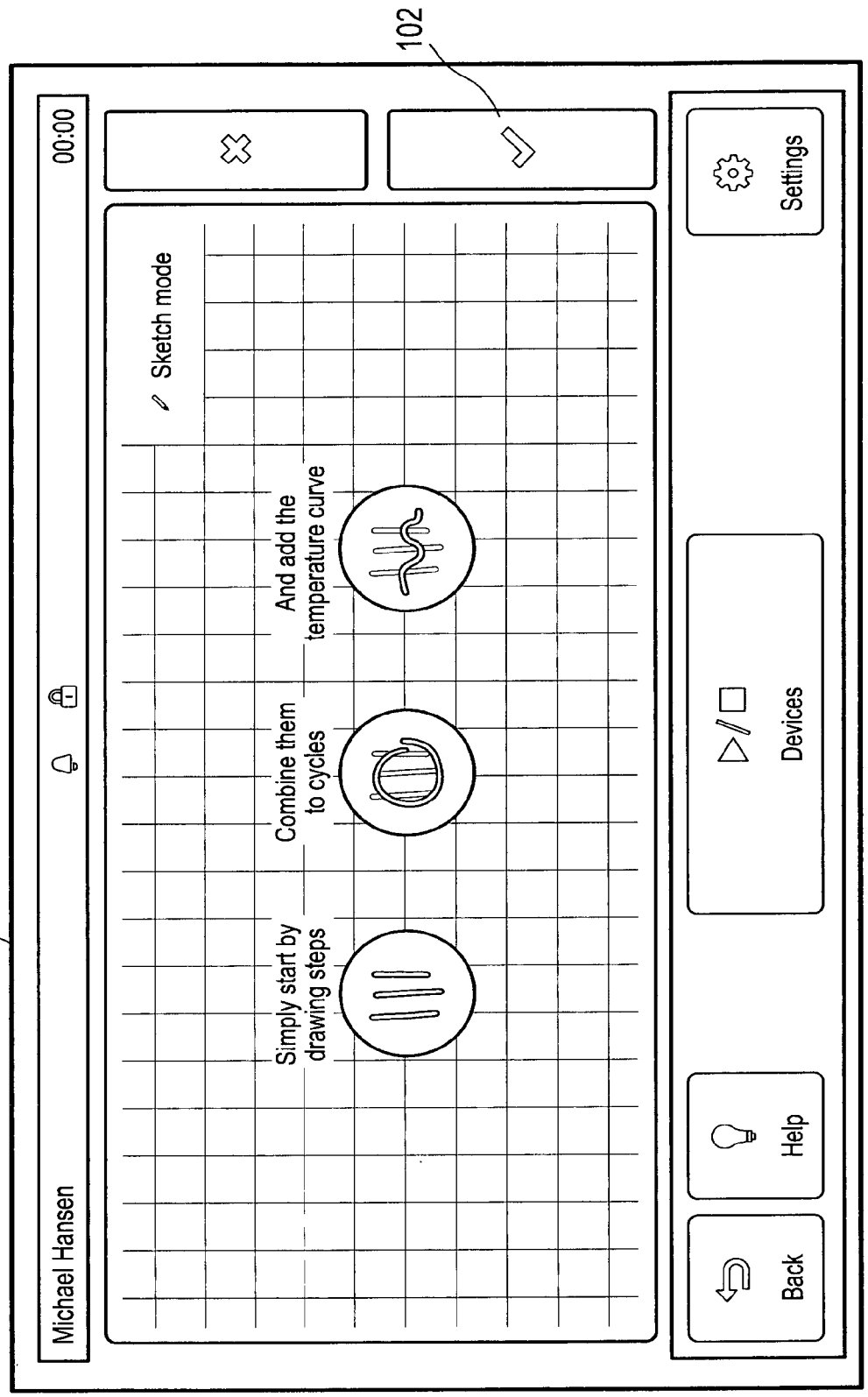
FIG. 2b illustrates the display area of a laboratory apparatus according to a first embodiment of the invention for the provision of a movement detecting input mode.

After activating the button 101, the user interface e.g. initially changes to a display as shown in FIG. 2b, in which explanations or rather auxiliary information about the movement detecting control mode are displayed, wherein the operating mode in the present case is configured so simple that the use of which is usually succeeded to users without performing a separated gesture training process. It is explained that three different types of typical user movements (gestures) are feasible for the input, namely horizontal movements by which program parameters are defined that refer to temperature levels as well as movements perpendicular thereto by which program parameters are defined that refer to time values, further circular selection movements, by which several graphical objects are selected for the definition of the content of a tempering cycle.

Figure 2C:
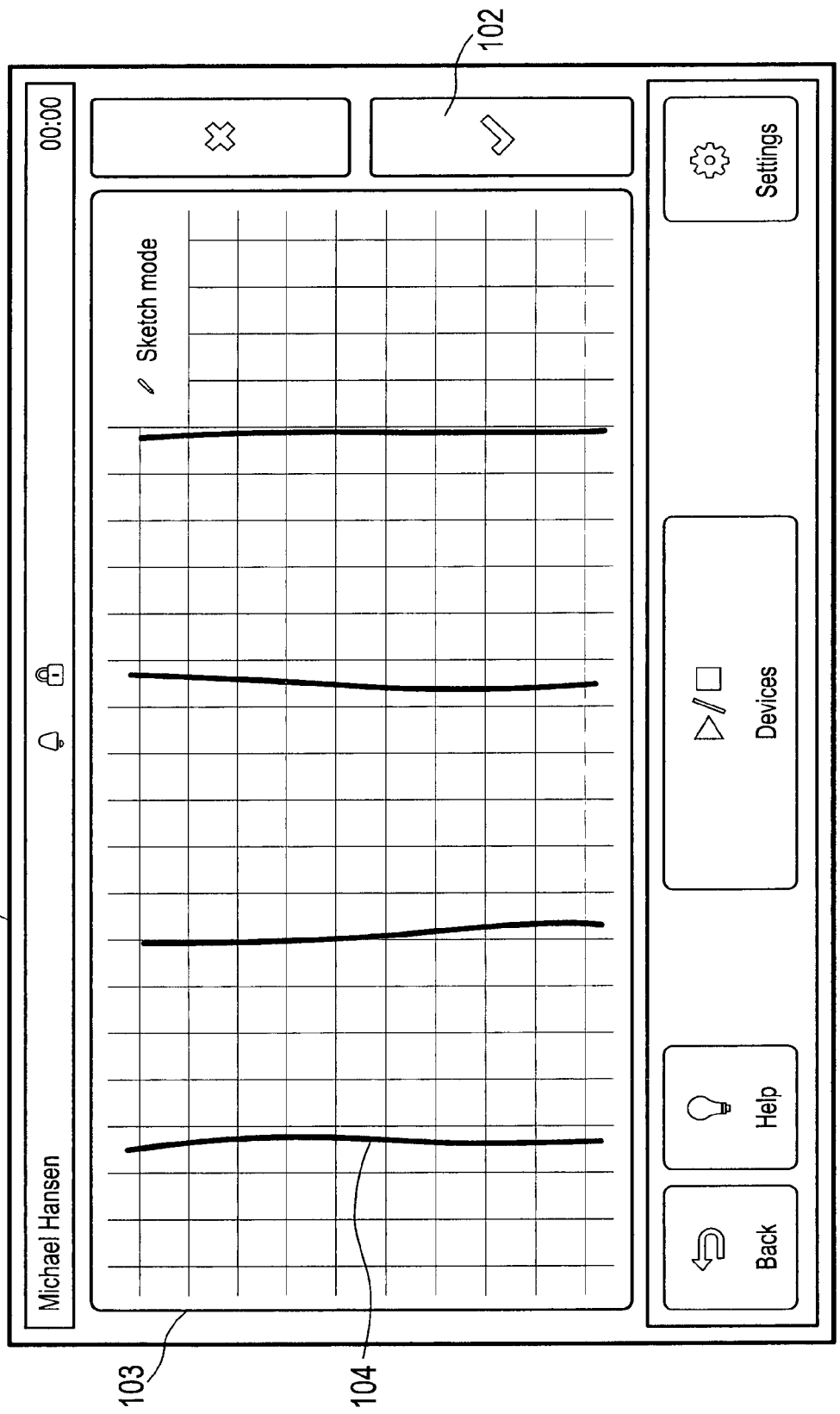
FIG. 2c illustrates the display area of a laboratory apparatus according to a third embodiment of the invention for the provision of a movement detecting input mode.

After confirming by touching the button 102, the display of the user interface illustrated in FIG. 2c is effected by the control device. There, a representation area 103 is displayed, which is usable as a drawing interface in the movement detecting input mode, on which the user can draw sketches, which correspond to the gestures. As will be explained, the extension of the representation area 103 in the horizontal direction along a virtual axis (x-axis) is used as a "time line" thereto, in order to enable the input of time values. The extension of the representation area 103 in a direction perpendicular to the horizontal direction along a further virtual axis (y-axis) as a "temperature axis" is used, in order to enable the input of temperature values.

Other movements, which are not detected as one of the possible gestures by the control device, lead to display a message to the user. In the representation area 103, four vertical linear sketch elements (vertical lines) 104 are displayed. Prior to this, these elements have been created by a user in the exact location on the display area of the display by detecting a linear vertical user movement in each case, which respectively contacts the display area and by displaying substantially without time delay, so that an intuitive work experience is set for the user.

Figure 2D:
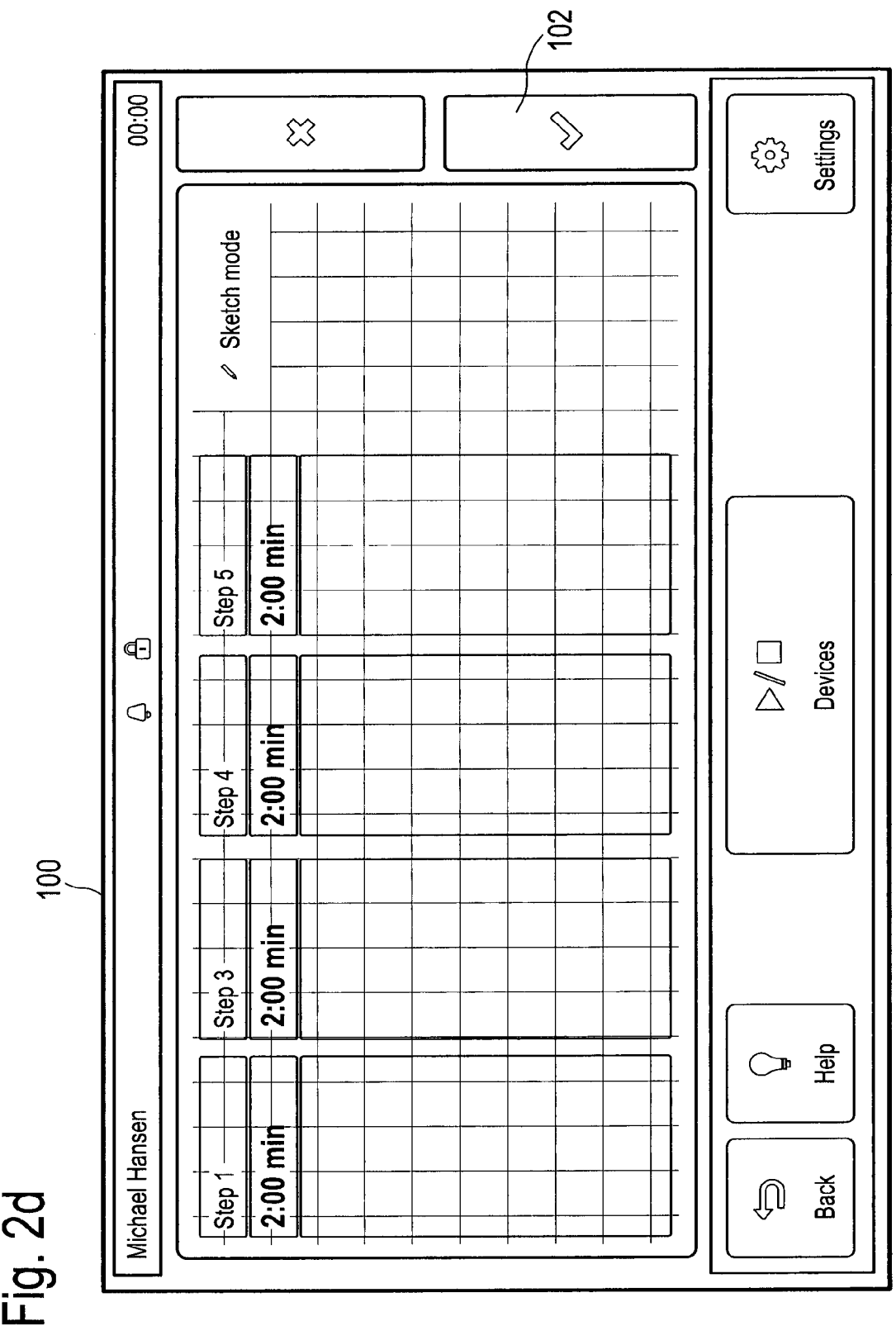
FIG. 2d illustrates the display area of a laboratory apparatus according to a fourth embodiment of the invention for the provision of a movement detecting input mode.
Figure 2E:
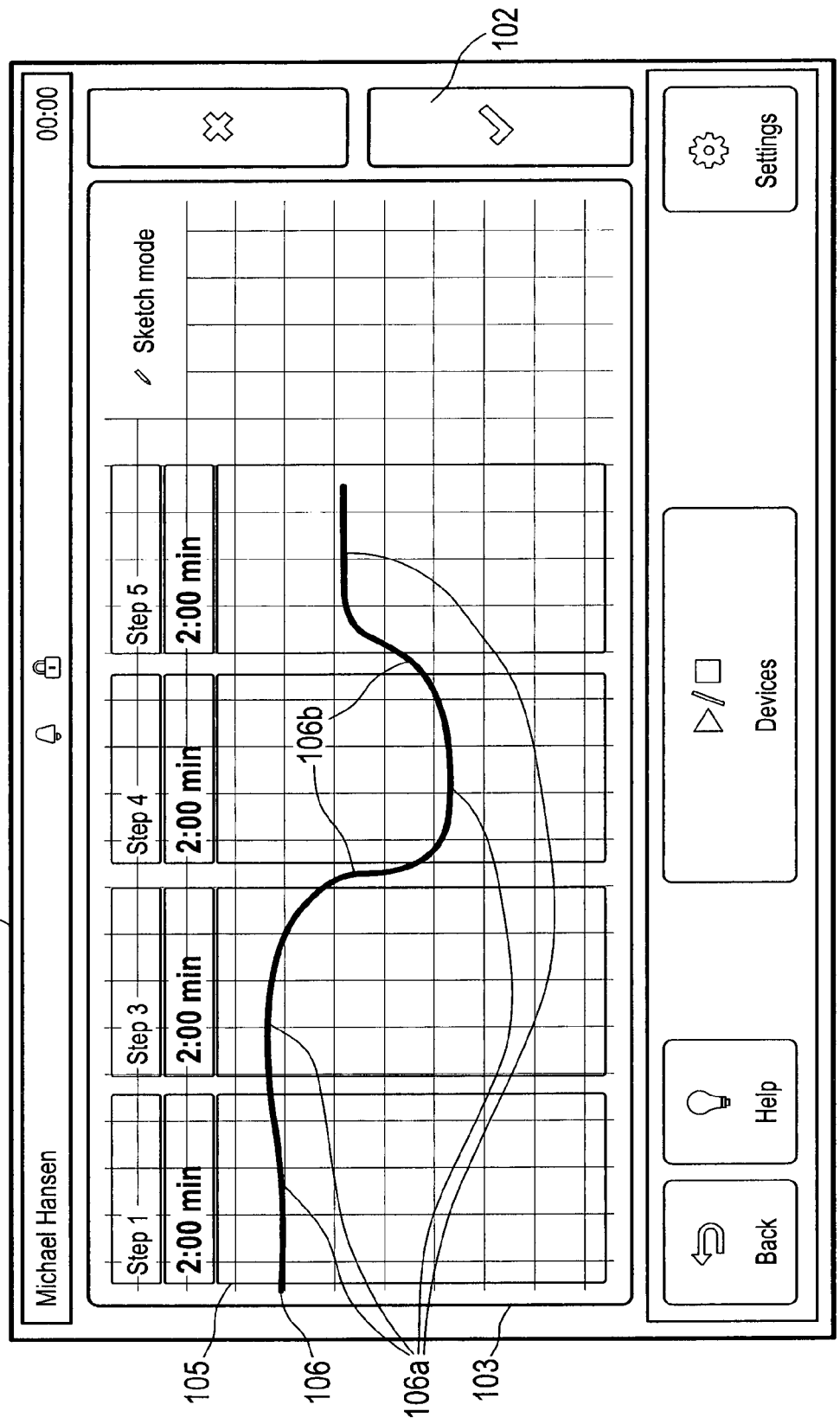
FIG. 2e illustrates the display area of a laboratory apparatus according to a fifth embodiment of the invention for the provision of a movement detecting input mode.

After confirming by touching the button 102, the display of the user interface illustrated in FIG. 2d is effected by the control device. There it is graphically illustrated, in which way the control device has used the user's four vertical gestures to the definition of program parameters forming time values. The first effort of the laboratory apparatus in the movement detecting input mode consists of the use of the "vertical" orientation of the user movement, in order to relate the input to the program parameter "time value". In the case of a horizontal movement performed by the user, the horizontal orientation would have been used, in order to relate the input to the program parameter "temperature value". Moreover, the number of totally four vertical stroke gestures performed in coexistence has been interpreted that in total four temperature levels are to be time-sequentially planned, wherein the default time period for the performance of tempering is on a temperature level at 2 minutes. The transition between the temperature levels occurs by default by means of the described ramps. The program parameter defined in this context thus relates to the number of tempering steps, which are to be performed consecutively at a temperature, which is still to be defined. Therefore, the program parameter implicitly relates to a time axis for the definition of the PCR process to be planned. As an alternative input form, a time axis would be possible, on which the user enters the start or rather the end of the tempering steps by means of vertical line gestures, e.g. detectable in temporal increments of 15 seconds. A tempering step in the present case is displayed as one of four subareas 105 laying side by side, which are superimposed over the representation area of the rectangular plane of the drawing 103. By default a time period of 2 minutes was used in this context.

Figure 2F:
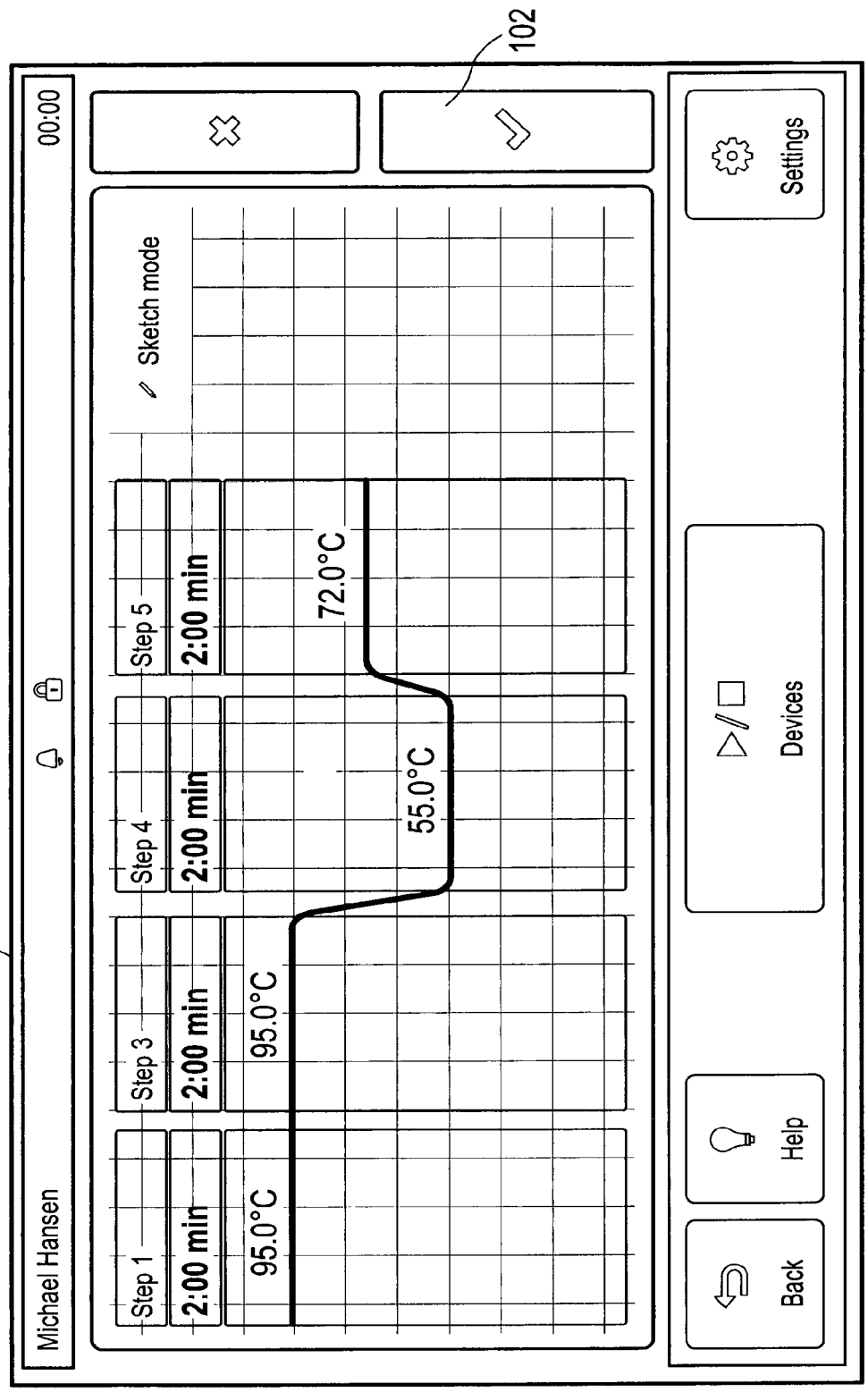
FIG. 2f illustrates the display area of a laboratory apparatus according to a sixth embodiment of the invention for the provision of a movement detecting input mode.

The user interface to the representation area 103 of FIG. 2d is used by the user as a new plane of the drawing. The user draws the curve 106 illustrated in FIG. 2e. The user performs a continuous curve on the rectangular plane of drawing 103, which comprises several horizontal segments 106a and curved portions 106b, which connect these horizontal segments. In the input mode, the horizontal segment 106a, which is drawn on the subarea 105, is automatically used in a period that refers to a subarea 105 for the definition of a temperature that is applied in this period. In FIG. 2f it is illustrated how the control device has taken the information, which refers to the consecutively following periods 105, from the curve 106, and therefore leads to the display of the temperatures of 95° C., 95° C., 55° C. and 72° C. in the idealized set-point temperature curve 106', which is illustrated in FIG. 2f in the representation area 103. The y-axis of the representation area is virtual and is initially structured in three vertically superimposed rectangular areas; a horizontal curve segment 106a in the uppermost section is automatically assigned to the temperature of 95° C., a horizontal curve segment 106a in the middle section is automatically assigned to the temperature of 72° C., a horizontal curve segment 106a in the lowermost section is automatically assigned to the temperature of 55° C. These three temperature values are default values, which can be later finely tuned by the user. In this context, the user can subsequently touch a horizontal section of the curve in FIG. 2e and change the temperature value associated with it (program parameters of this temperature section). This can e.g. be technically implemented so that the user can shift the horizontal curve section, wherein then the modified associated temperature value is numerically displayed to him "live", on reaching the desired temperature value, the user disengages the curve, he terminates the corresponding movement. Thus, from the curve 106 pairs of values are obtained, consisting of period number (or time interval respectively) and temperature level.

Figure 2G:
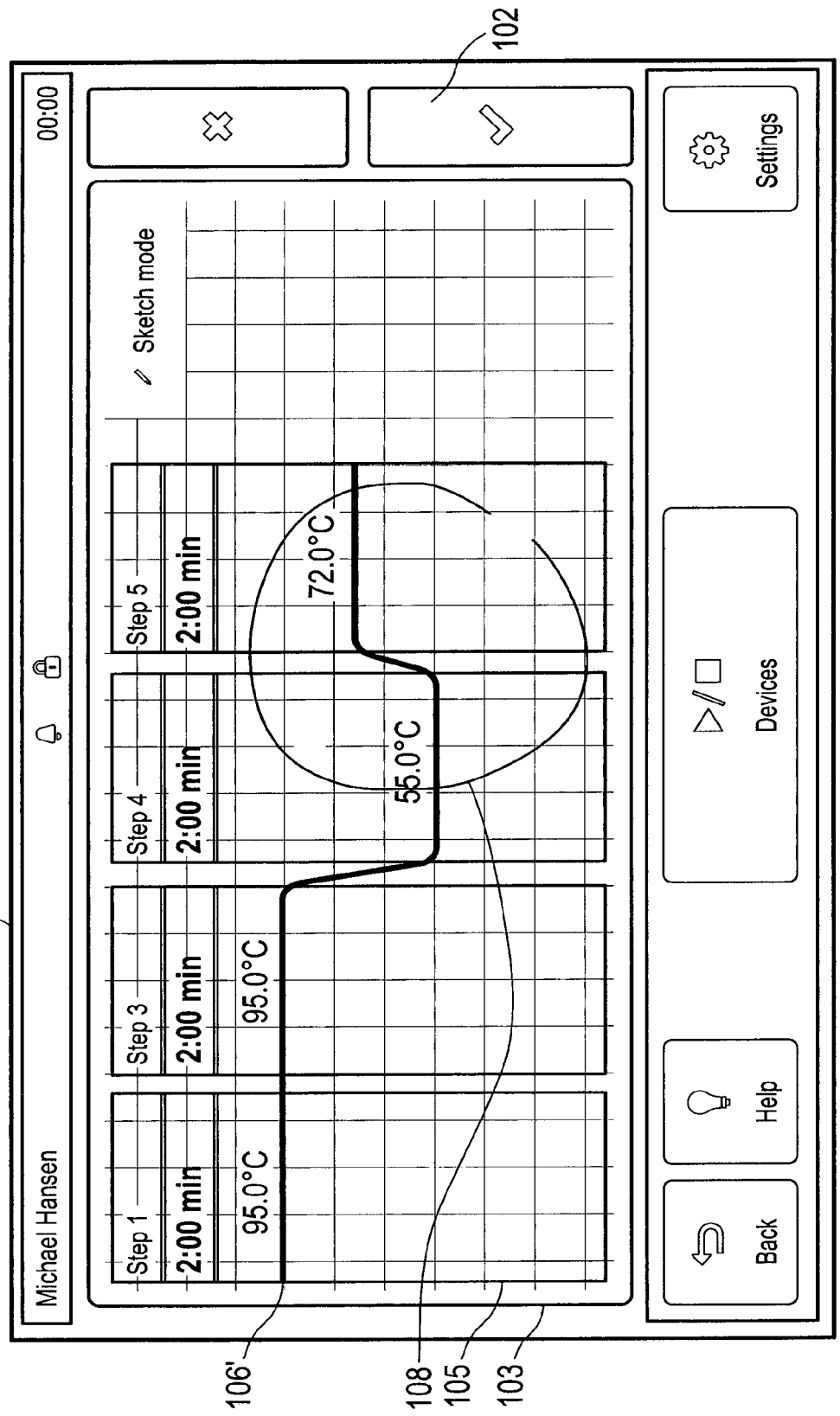
FIG. 2g illustrates the display area of a laboratory apparatus according to a seventh embodiment of the invention for the provision of a movement detecting input mode.

In FIG. 2g it is illustrated, in which way the control device by means of a substantially circular selection movement of the user, displayed as a substantially graphical sketch element 108, provides for several pairs of values, comprising period number and temperature level, for the definition of a PCR cycle. In the present case, the user simply indicates by the circle two sections 105 of the representation area 103 in the display area 100. Thus, the program parameters associated with that program area are selected and are introduced into the following program step, in which the user requests the number A of the desired repetitions of the cycle.

Figure 2H:
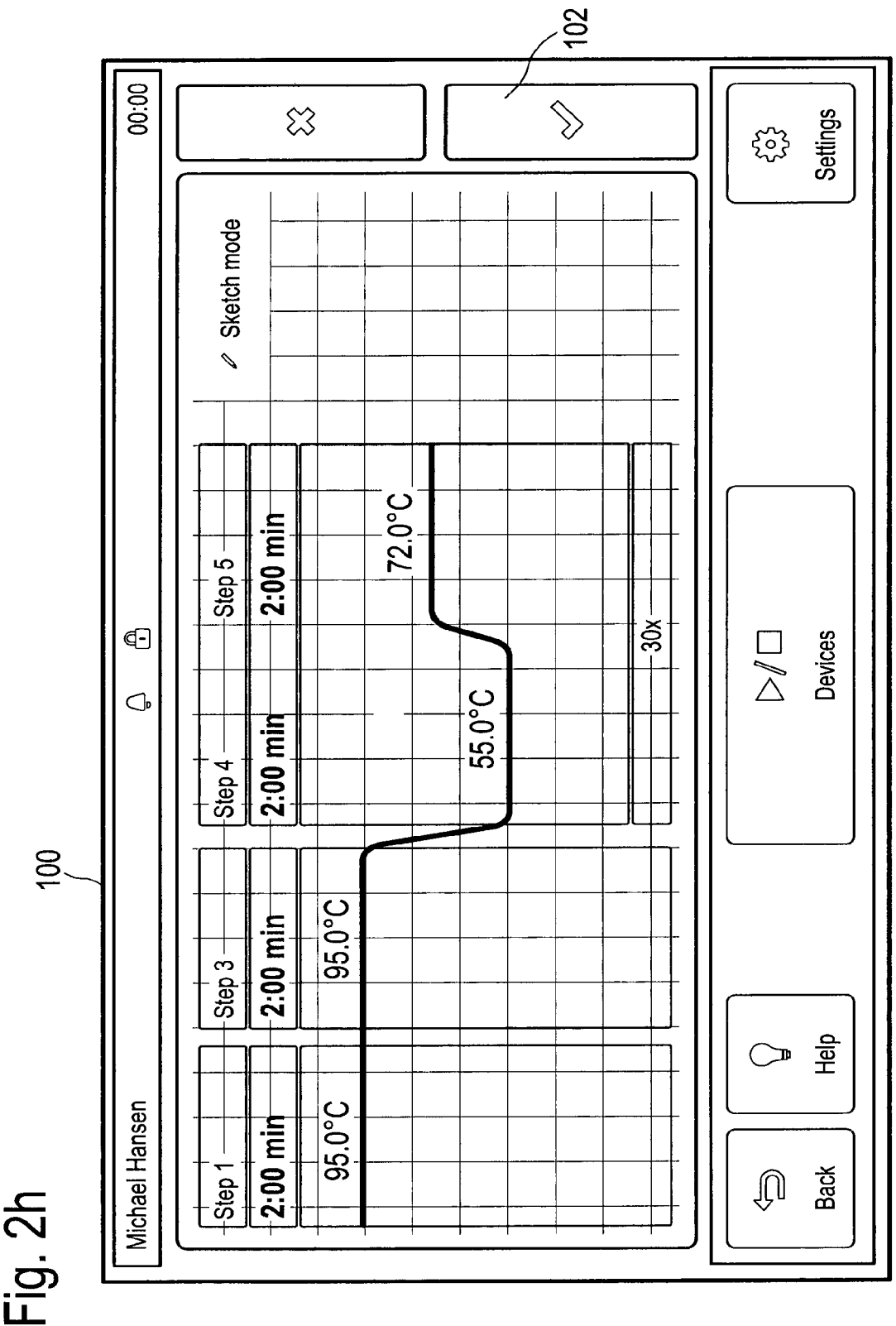
FIG. 2h illustrates the display area of a laboratory apparatus according to an eighth embodiment of the invention for the provision of a movement detecting input mode.

In FIG. 2h, the completely planned PCR process is illustrated graphically, in which it is highlighted that the last defined cycle having two pairs of values (time interval, temperature level) should be repeated A=30 times.

The input option developed in this way leads to a user-friendly, intuitive operation of laboratory apparatus and to an efficient, low-error workflow.

Figure 3:
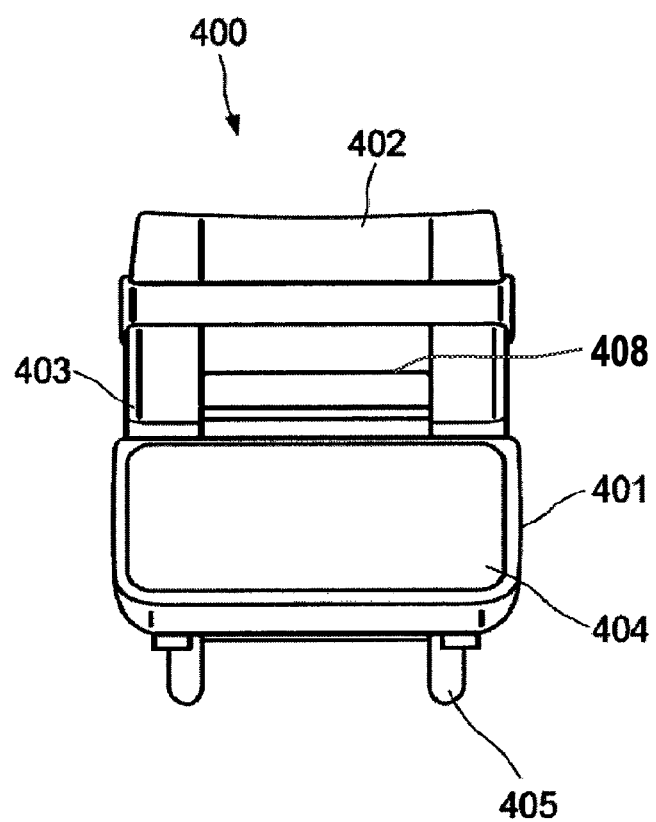
FIG. 3 illustrates a further exemplary embodiment of the laboratory apparatus according to the invention, a thermal cycler.

FIG. 3 illustrates a laboratory apparatus 400, a thermal cycler, configured for the automated processing of liquid samples, in particular for the program-controlled tempering of liquid samples. The laboratory apparatus 400 is a tabletop unit. It disposes of an integrated electronic control device 406 (not shown), which is adapted for processing a program code for program-controlled handling of liquid samples. The control device 406 is accommodated in the housing 401. The housing also accommodates the power supply components that supply the appropriate supply voltage for the electrical components of the thermal cycler.

The laboratory apparatus 400 comprises a handling chamber 403 for the accommodation of the liquid samples to be handled, which can accommodate at least one program-controlled controllable handling device 408, for performing of at least one program-controlled handling step at the at least one sample, which is arranged in the handling device, which is arranged in the processing chamber. The handling chamber can be closed by a lid 402, in order to create a defined tempering environment. In FIG. 4, the laboratory apparatus is illustrated in a closed condition. The control device 406 comprises a control program.

The laboratory apparatus comprises a user interface device, namely a touch screen 404 for the manual input of data by a user, and for the display of information, which may particularly be dependent on these data, wherein the user interface device comprises a display, on which a display area can be displayed. The touch screen 404 comprises a movement detecting sensor device (not visible), which is arranged for the detection of at least one user movement, which can be performed at the display area by a user. The control device is arranged for the provision of a movement detecting input mode, in order to select the at least on program parameter and/or to define its value depending on the at least one user movement, and to display at least one graphical sketch element, which represents at least one user movement, depending on the at least one user movement in the display area. The thermal cycler 404 is particularly configured for achieving the configurations shown in FIGS. 2a to 2h, and in particular for realizing a movement detecting input mode, such as described with reference to FIGS. 2a to 2h.

The invention claimed is:
1. A laboratory apparatus (1) for device-controlled handling of at least one laboratory sample, comprising:
at least one handling device for program-controlled handling of the at least one laboratory sample, wherein the program-controlled handling uses program parameters, which are at least partly defined as user parameters by a user, are controlled by the laboratory apparatus,
a control device, comprising at least one processor device for data processing, wherein this data processing includes the execution of a control program for controlling the laboratory apparatus, and comprising at least one storage device for storing data, the control program and the program parameters,
a user interface device (5) configured for the manual input of user data by a user, and for the display of information, the information depending on the user data,
wherein the user interface device comprises a display, on which a display area (100) can be displayed, the display area containing a representation area being usable as a drawing interface, on which the user can draw sketches, in a movement detecting input mode provided by the control device, and
wherein the user interface device comprises a movement detecting sensor device, which is arranged for the detection of at least one user movement, which is performable on the display area by a user, and
wherein the control device, for providing the movement detecting input mode, is programmed
to detect the at least one user movement being a continuous curve on the display area by means of the movement detecting sensor device;
to determine the movement information from this user movement in the form of movement data and to store the movement data in the at least one storage device;
to provide a visual monitoring of the user movement by displaying, without an observable time delay for the user, at least one graphical sketch element, which is a graphical object being a path, which represents the at least one user movement and which is drawn by the user in the representation area of the display while performing the at least one user movement,
after displaying the graphical sketch element, to select at least one program parameter of the program parameters and/or to define a value of at least one program parameter of the program parameters depending on the at least one user movement and the movement data; and to detect pairs of program parameters or pairs of values of one program parameter or of two program parameters, which are represented in the display area as a point sequence or as a curve at two axis perpendicularly oriented to each other, in the movement detecting input mode by the user movement, wherein this point sequence or this curve forms the path.

2. The laboratory apparatus according to claim 1, characterized in that the movement detecting input mode provides for displaying potential values of at least one first program parameter along a first linear axis in the display area and for detecting a user movement perpendicular to the one first linear axis in this input mode, in order to select the at least one program parameter being associated with the first linear axis and/or to define the value of the at least one program parameter associated with the first linear axis.

3. The laboratory apparatus according to claim 2, characterized in that the movement detecting input mode provides for displaying potential values of at least one second program parameter along a second linear axis in the display area and for detecting a user movement perpendicular to the one second linear axis in this input mode, in order to select the at least one program parameter to be associated with the second linear axis and/or to define the value of the at least one program parameter associated with the second linear axis.

4. The laboratory apparatus according to claim 2, characterized in that the control device in the movement detecting input mode is arranged for detecting a position of the user movement perpendicular to the first linear axis, wherein this position is characteristic for the value of the at least one program parameter associated with the first linear axis.

5. The laboratory apparatus according to claim 2, characterized in that the control device is arranged for incrementally providing the input of a value by the positional detection of the user movement perpendicular to the first linear axis.

6. The laboratory apparatus according to claim 1, characterized in that the control device is arranged for displaying several graphical objects in the display area during the movement detecting input mode, wherein each object represents a program parameter or a value of a program parameter, and for using a substantially circular user movement, which at least contacts and/or frames one or more of these graphical objects, as a selected movement, with which the several program parameters or their values are selected.

7. The laboratory apparatus according to claim 1, characterized in that the user interface device comprises at least one further input device, and that the control device is arranged for enabling a further change of the at least one program parameter or its value by means of the at least one further input device, after the at least one program parameter or its value was selected and/or defined by the at least one user movement.

8. The laboratory apparatus according to claim 1, which is a thermal cycler.

9. The laboratory apparatus according to claim 1, which is a pipetting machine.

10. The pipetting machine according to claim 9, wherein the control device is arranged for using an input by means of the at least one user movement in such a way to manually define a pipetting pattern.

11. The laboratory apparatus of claim 2, the at least one first program parameter being a time value.

12. The laboratory apparatus of claim 3, the at least one second program parameter being a temperature.

13. A method for detecting at least one user input in an input mode of a laboratory apparatus, which is configured according to claim 1, comprising the steps of:

Detecting at least one user movement on the display area by means of the movement detecting sensor device;

Defining at least one program parameter and/or its value depending on the at least one user movement, Displaying a graphical sketch element, which is a graphical object being a path, which represents the at least one user movement.

\* \* \* \* \*